(12) United States Patent  
Babu et al.

(10) Patent No.: US 9,250,236 B2  
(45) Date of Patent: Feb. 2, 2016

(54) METHOD TO INCREASE SPECIFICITY AND/OR ACCURACY OF LATERAL FLOW IMMUNOASSAYS

(71) Applicant: Rapid Pathogen Screening, Inc, Sarasota, FL (US)

(72) Inventors: Uma Mahesh Babu, Bradenton, FL (US); Franz Aberl, Kranzberg (DE); Marcus Scheibenzuber, Munich (DE); Robert P. Sambursky, Bradenton, FL (US); Robert W. VanDine, Montoursville, PA (US); Jose S. Sambursky, Long Boat Key, FL (US)

(73) Assignee: Rapid Pathogen Screening, Inc., Sarasota, FL (US)

( * ) Notice: Subject to any disclaimer, the term of this patent is extended or adjusted under 35 U.S.C. 154(b) by 504 days.

(21) Appl. No.: 13/800,114

(22) Filed: Mar. 13, 2013

(65) Prior Publication Data

US 2013/0295583 A1 Nov. 7, 2013

Related U.S. Application Data

(60) Division of application No. 12/568,970, filed on Sep. 29, 2009, now Pat. No. 8,445,293, which is a continuation-in-part of application No. 11/052,748, filed on Feb. 9, 2005, now Pat. No. 7,723,124, and acontinuation-in-part of application No. 11/224,298, filed on Sep. 13, 2005, now abandoned, and a contin- (Continued)

(51) Int. Cl.
*G01N 33/558* (2006.01)
*G01N 33/543* (2006.01)
*G01N 33/68* (2006.01)

(52) U.S. Cl.
CPC .... *G01N 33/54393* (2013.01); *G01N 33/54386* (2013.01); *G01N 33/558* (2013.01);

(Continued)

(58) Field of Classification Search
None
See application file for complete search history.

(56) References Cited

U.S. PATENT DOCUMENTS

| 4,094,647 A | 6/1978 | Deutsch et al. |
| 4,299,916 A | 11/1981 | Litman et al. |

(Continued)

FOREIGN PATENT DOCUMENTS

| DE | 4439429 C2 | 11/1997 |
| DE | 19622503 C2 | 12/1997 |

(Continued)

OTHER PUBLICATIONS

Scantibodies Laboratories website, http://web.archive.org/web/20071013114943/scantibodies.com/block.html (Jun. 13, 2008).

(Continued)

*Primary Examiner* — Chris L Chin
(74) *Attorney, Agent, or Firm* — Brown & Michaels, PC

(57) ABSTRACT

The present invention includes methods and devices for preventing interfering substances from affecting the accuracy of a lateral flow immunoassay. In preferred embodiments, a test strip includes a capturing zone that includes at least one mobile capturing reagent that separates at least one interfering substance from the analyte. The capturing zone is preferably located upstream of the sample application zone. In some embodiments, the reagent/conjugate zone is also located upstream of the sample application zone. The capturing zone may be located upstream, downstream, or overlapping with the reagent/conjugate zone in these embodiments. In other preferred embodiments, one or more mobile capturing reagents are included in the elution medium/running buffer. In yet other embodiments, the capturing reagent is incorporated into a sample collection device of a sample collection system, preferably separate from the chromatographic test strip. A lysis zone is also included in some preferred embodiments.

8 Claims, 13 Drawing Sheets

Related U.S. Application Data uation-in-part of application No. 11/698,053, filed on Jan. 26, 2007, now abandoned, and a continuation-in-part of application No. 12/469,207, filed on May 20, 2009, now abandoned, said application No. 12/568,970 is a continuation-in-part of application No. 12/481,631, filed on Jun. 10, 2009, now Pat. No. 8,470,608, said application No. 12/568,970 is a continuation-in-part of application No. 12/502,626, filed on Jul. 14, 2009, now Pat. No. 8,669,052, and a continuation-in-part of application No. 12/502,662, filed on Jul. 14, 2009, now Pat. No. 8,614,101.

(60) Provisional application No. 61/179,059, filed on May 18, 2009, provisional application No. 61/071,833, filed on May 20, 2008, provisional application No. 61/060,258, filed on Jun. 10, 2008, provisional application No. 61/080,879, filed on Jul. 15, 2008, provisional application No. 61/098,935, filed on Sep. 22, 2008.

(52) U.S. Cl.
CPC ... *G01N33/6893* (2013.01); *Y10T 436/142222* (2015.01); *Y10T 436/173845* (2015.01); *Y10T 436/25* (2015.01); *Y10T 436/25125* (2015.01); *Y10T 436/25375* (2015.01)

(56) References Cited

U.S. PATENT DOCUMENTS

| | | | |
|---|---|---|---|
| 4,362,531 A | 12/1982 | de Steenwinkel et al. |
| 4,508,892 A | 4/1985 | Yoshida |
| 4,737,456 A | 4/1988 | Weng et al. |
| 4,764,459 A | 8/1988 | Hampar et al. |
| 4,810,635 A | 3/1989 | Ledden et al. |
| 4,844,866 A | 7/1989 | Wallace et al. |
| 4,857,453 A | 8/1989 | Ullman et al. |
| 4,904,448 A | 2/1990 | Kawahara |
| 4,960,691 A | 10/1990 | Gordon et al. |
| 4,968,633 A | 11/1990 | Marcucci |
| 5,026,653 A | 6/1991 | Lee et al. |
| 5,030,561 A | 7/1991 | Mapes et al. |
| 5,075,078 A | 12/1991 | Osikowicz et al. |
| 5,120,643 A | 6/1992 | Ching et al. |
| 5,403,745 A | 4/1995 | Ollington et al. |
| 5,413,911 A | 5/1995 | Adamczyk et al. |
| 5,451,504 A | 9/1995 | Fitzpatrick et al. |
| 5,571,723 A | 11/1996 | Evans et al. |
| 5,591,645 A | 1/1997 | Rosenstein |
| 5,607,863 A | 3/1997 | Chandler |
| 5,698,393 A | 12/1997 | Macioszek et al. |
| 5,705,353 A | 1/1998 | Oh et al. |
| 5,714,341 A | 2/1998 | Thieme et al. |
| 5,714,389 A | 2/1998 | Charlton et al. |
| 5,731,162 A | 3/1998 | Gatti et al. |
| 5,766,552 A | 6/1998 | Doshi et al. |
| 5,798,273 A | 8/1998 | Shuler et al. |
| 5,804,391 A | 9/1998 | Klemt et al. |
| 5,863,740 A | 1/1999 | Kientsch-Engel et al. |
| 5,939,331 A | 8/1999 | Burd et al. |
| 5,945,345 A | 8/1999 | Blatt et al. |
| 5,965,378 A | 10/1999 | Schlieper et al. |
| 5,989,921 A | 11/1999 | Charlton et al. |
| 5,998,220 A | 12/1999 | Chandler |
| 6,010,866 A | 1/2000 | Ollington et al. |
| 6,017,767 A | 1/2000 | Chandler |
| 6,046,058 A | 4/2000 | Sun |
| 6,087,088 A | 7/2000 | Piran et al. |
| 6,087,184 A | 7/2000 | Magginetti et al. |
| 6,127,130 A | 10/2000 | Brizzolara |
| 6,146,589 A | 11/2000 | Chandler |
| 6,153,393 A | 11/2000 | Seidel et al. |
| 6,168,956 B1 | 1/2001 | Chandler |
| 6,187,598 B1 | 2/2001 | May et al. |
| 6,221,678 B1 | 4/2001 | Chandler |
| 6,284,550 B1 | 9/2001 | Carroll et al. |
| 6,331,402 B1 | 12/2001 | Nussbaum et al. |
| 6,375,896 B1 | 4/2002 | Wuske et al. |
| 6,406,858 B1 | 6/2002 | Petry et al. |
| 6,485,982 B1 | 11/2002 | Charlton |
| 6,489,131 B1 | 12/2002 | Wehner et al. |
| 6,498,010 B1 | 12/2002 | Fitzgerald et al. |
| 6,514,773 B1 | 2/2003 | Klein et al. |
| 6,528,322 B1 | 3/2003 | Carlsson et al. |
| 6,548,309 B1 | 4/2003 | Moore et al. |
| 6,555,390 B2 | 4/2003 | Chandler |
| 6,663,833 B1 | 12/2003 | Stave et al. |
| RE38,430 E | 2/2004 | Rosenstein |
| 6,703,196 B1 | 3/2004 | Klepp et al. |
| 6,716,641 B1 | 4/2004 | Sundrehagen |
| 6,737,278 B1 | 5/2004 | Carlsson et al. |
| 6,890,484 B2 | 5/2005 | Bautista et al. |
| 7,109,042 B2 | 9/2006 | May et al. |
| 7,300,750 B2 | 11/2007 | Smart et al. |
| 7,354,614 B2 | 4/2008 | Quinlan et al. |
| 7,374,950 B2 | 5/2008 | Kang et al. |
| 7,384,598 B2 | 6/2008 | Quirk et al. |
| 7,387,890 B2 | 6/2008 | Esfandiari |
| 7,393,697 B2 | 7/2008 | Charlton |
| 7,425,302 B2 | 9/2008 | Piasio et al. |
| 7,465,587 B2 | 12/2008 | Imrich |
| 7,569,397 B2 | 8/2009 | Esfandiari |
| 2002/0036170 A1 | 3/2002 | Harvey et al. |
| 2003/0049658 A1 | 3/2003 | Smart et al. |
| 2003/0104506 A1 | 6/2003 | Durst et al. |
| 2003/0119083 A1 | 6/2003 | Owens et al. |
| 2003/0166291 A1 | 9/2003 | Jones et al. |
| 2003/0232451 A1 | 12/2003 | Casterlin et al. |
| 2004/0023412 A1 | 2/2004 | Carlsson et al. |
| 2004/0082077 A1 | 4/2004 | Hu |
| 2004/0115831 A1 | 6/2004 | Meathrel et al. |
| 2004/0152142 A1 | 8/2004 | Klepp et al. |
| 2004/0161857 A1 | 8/2004 | Yugawa et al. |
| 2004/0235189 A1 | 11/2004 | Lu |
| 2004/0241779 A1 | 12/2004 | Piasio et al. |
| 2005/0142622 A1 | 6/2005 | Sanders et al. |
| 2005/0147532 A1 | 7/2005 | Bellet et al. |
| 2005/0148097 A1 | 7/2005 | Mizukami |
| 2005/0181517 A1 | 8/2005 | Chandler et al. |
| 2005/0244986 A1 | 11/2005 | May et al. |
| 2006/0003390 A1 | 1/2006 | Schaffler et al. |
| 2006/0024767 A1 | 2/2006 | Hajizadeh et al. |
| 2006/0121626 A1 | 6/2006 | Imrich |
| 2006/0172434 A1 | 8/2006 | Rowell |
| 2006/0223192 A1 | 10/2006 | Smith et al. |
| 2007/0224701 A1 | 9/2007 | Rosenstein |
| 2009/0011436 A1 | 1/2009 | Piasio et al. |
| 2009/0253119 A1 | 10/2009 | Zhou et al. |

FOREIGN PATENT DOCUMENTS

| | | |
|---|---|---|
| EP | 0306772 A1 | 3/1989 |
| EP | 0699906 B1 | 3/1996 |
| JP | 63501074 | 4/1988 |
| JP | 9171019 | 6/1997 |
| JP | 2002340897 | 5/2001 |
| JP | 2002539425 | 11/2002 |
| JP | 2005529305 | 9/2005 |
| WO | 9415215 A1 | 7/1994 |
| WO | 9960402 A1 | 4/1999 |
| WO | 9936776 A1 | 7/1999 |
| WO | 0054024 A1 | 3/2000 |
| WO | 0136975 A1 | 5/2001 |
| WO | 2004076054 A2 | 9/2004 |
| WO | 2007070117 A1 | 6/2007 |
| WO | 2007110779 A2 | 10/2007 |

OTHER PUBLICATIONS

Uchio et al., "Rapid Diagnosis of Adenoviral Conjunctivitis on Conjunctival Swabs by 10-Minute Immunochromatography", Ophthalmology 104, 1294-1299 (1997).

(56) References Cited

OTHER PUBLICATIONS

Bruning et al., "A rapid chromatographic strip test for the pen-side diagnosis of rinderpest virus", Journal of Virological Methods, 81, 143-154 (1999).

Toraason et al., "Latex Allergy in the Workplace", Toxicological Sciences, 58, 5-14 (2000).

Wambura et al., "Diagnosis of Rinderpest in Tanzania by a Rapid Chromatographic Strip-test", Tropical Animal Health and Production, 32, 141-145 (2000).

Sobanski et al., "Detection of adenovirus and rotavirus antigens by an immuno-gold lateral flow test and ultrasound-enhanced latex agglutination assay", Journal of Medical Microbiology, 50, 203 (2001).

Udeh et al., "Cost Effectiveness of a Point-of-Care Test for Adenoviral Conjunctivitis", The American Journal of the Medical Sciences, vol. 336, No. 3, pp. 254-264 (Sep. 2008).

Kent, ed., "Point-of-Care Screening for Conjunctivitis", Review of Ophthalmology, vol. 12, Iss. 4, http://www.revophth.com/index.asp?page=1_707.htm (Apr. 15, 2005).

"Rapid test for pink eye may curb overuse of antibiotics", http://www.stjohns.com/news/pinkeyetest.aspx (Jan. 26, 2009).

Sambursky et al., "The RPS Adeno Detector for Diagnosing Adenoviral Conjunctivitis", Ophthalmology, vol. 113, No. 10, pp. 1758-1764 (Oct. 2006).

Sambursky, "Physicians Guide to RPS Adeno DetectorTM", http://www.eyecaresource.com/conditions/pink-eye/physician-guide.html.

Sambursky, "501-K Summary of Safety and Effectiveness" (Sep. 14, 2005).

Sevier et al, "Monoclonal Antibodies in Clinical Immunology", Clin. Chem. 27/11, 1981, pp. 1797-1806.

METHOD TO INCREASE SPECIFICITY AND/OR ACCURACY OF LATERAL FLOW IMMUNOASSAYS

REFERENCE TO RELATED APPLICATIONS

This is a divisional patent application of application Ser. No. 12/568,970, filed Sep. 29, 2009, entitled "METHOD TO INCREASE SPECIFICITY AND/OR ACCURACY OF LATERAL FLOW IMMUNOASSAYS", now issued U.S. Pat. No. 8,445,293, which claims one or more inventions which were disclosed in Provisional application No. 61/179,059, filed May 18, 2009, entitled "METHOD AND DEVICE FOR COMBINED DETECTION OF VIRAL AND BACTERIAL INFECTIONS".

This application is also a continuation-in-part application of application Ser. No. 11/052,748, filed Feb. 9, 2005, entitled "METHOD FOR THE RAPID DIAGNOSIS OF TARGETS IN HUMAN BODY FLUIDS", now issued U.S. Pat. No. 7,723,124, application Ser. No. 11/224,298, filed Sep. 13, 2005, entitled "METHOD TO INCREASE SPECIFICITY AND/OR ACCURACY OF LATERAL FLOW IMMUNOASSAYS", now abandoned, application Ser. No. 11/698,053, filed Jan. 26, 2007, entitled "METHOD FOR THE RAPID DIAGNOSIS OF TARGETS IN HUMAN BODY FLUIDS", application Ser. No. 12/469,207, filed May 20, 2009, entitled "NANOPARTICLES IN DIAGNOSTIC TESTS", now abandoned, which claimed priority from Provisional Application No. 61/071,833, filed May 20, 2008, entitled "NANOPARTICLES IN DIAGNOSTIC TESTS", copending application Ser. No. 12/481,631, filed Jun. 10, 2009, entitled "COMBINED VISUAL/FLUORESCENCE ANALYTE DETECTION TEST", which claimed priority from Provisional Application No. 61/060,258, filed Jun. 10, 2008, entitled "COMBINED VISUAL/FLUORESCENCE ANALYTE DETECTION TEST", copending application Ser. No. 12/502,626, filed Jul. 14, 2009, which claimed priority from Provisional Application No. 61/080,879, filed Jul. 15, 2008, entitled "LATERAL FLOW NUCLEIC ACID DETECTOR", and Provisional Application No. 61/098,935, filed Sep. 22, 2008, entitled "IN SITU LYSIS OF CELLS IN LATERAL FLOW IMMUNOASSAYS", and application Ser. No. 12/502,662, filed Jul. 14, 2009, entitled "IN SITU LYSIS OF CELLS IN LATERAL FLOW IMMUNOASSAYS".

The benefit under 35 USC §119(e) of the United States provisional applications are hereby claimed, and the aforementioned applications are hereby incorporated herein by reference.

BACKGROUND OF THE INVENTION

1. Field of the Invention

The invention pertains to the field of immunoassays. More particularly, the invention pertains to methods and devices for increasing specificity and/or accuracy of lateral flow immunoassays.

2. Description of Related Art

Lateral flow immunoassays are a subset of antibody-based immunoassays combining various reagents and process steps in one assay strip, thus providing a sensitive and rapid means for the detection of target molecules. Lateral flow immunoassays are available for a wide area of target analytes and can be designed for sandwich or competitive test principles. Generally high molecular weight analytes with several epitopes are analyzed in a sandwich format whereas small molecules representing only one epitope are detected by means of a competitive assay. The first tests were made for human chorionic gonadotropin (hCG). Today there are commercially available tests for monitoring ovulation, detecting infectious disease organisms, analyzing drugs of abuse and measuring other analytes important to human physiology. Products have also been introduced for veterinary testing, environmental testing and product monitoring.

U.S. Pat. No. 5,714,341 discloses a lateral flow immunoassay for HIV specific antibodies in saliva samples. The saliva sample is diluted in a sample buffer and the lateral flow immunoassay is dipped into the diluted saliva sample. The disclosure of this document is herein incorporated by reference.

German Patent DE 196 22 503 discloses methods for detecting illegal narcotics on a surface using lateral flow immunoassays. The disclosure of this document is herein incorporated by reference.

The growing use of antibody based immunoassays in recent years has required increased effort and investigation on minimizing interferences found in many samples. A typical problem is the presence of interfering substances, e.g. antibodies, in whole blood, serum and other human fluid samples. These interfering antibodies can be divided into auto-antibodies or rheumatoid factors (RF), heterophilic antibodies and human anti-mouse antibodies (HAMA).

Auto-antibodies or rheumatoid factors (RF) show anti-IgG activity and are predominantly composed of the IgM class. Most often they recognize the Fc region of the antigen bound IgG antibodies. Rheumatoid factor antibodies may also be of the IgG and IgA classes and have been observed reacting with antibodies of the IgM class. To further complicate this group of interfering antibodies, rheumatoid factors from one species may react with immunoglobulins of another species.

Heterophilic antibodies are one of many sources of interference in immunoassays. This often-misapplied term was historically used to refer to certain populations of antibodies in patient sera, which caused the aggregation of sheep red blood cells, and observed to be associated with Epstein-Barr virus (EBV) infections. In immunoassay development labs today, the term heterophile is frequently used to describe an interfering antibody (or other binding molecule) which has an unknown origin. These relatively common low affinity antibodies occur in approximately 1-5% of the healthy human population and effectively compete with the analyte of interest, which may produce abnormally high or false positive immunoassay results.

Human anti-mouse antibodies (HAMA) are high affinity human anti-animal antibodies, which are directed against specific animal immunoglobulins. Human anti-mouse antibodies have been reported to give false positive results in sandwich immunoassays that utilize mouse monoclonal IgG. HAMA reactivity has been detected in approximately 9% of the normal human population. In this segment of the population, the patient sample contains an antibody to mouse immunoglobulin due to a previous exposure to mouse antibodies. This can occur through diet or through exposure, or may be a direct result of monoclonal antibody therapy—a presently uncommon, but growing subset of the patient population. Actually, not all HAMAs are human anti-mouse antibodies. Many are other animals, such as, for example anti-rabbit antibodies or anti-dog antibodies. Since immunoglobulins are highly conserved across species, it is not uncommon to see a patient with an antibody titer to immunoglobulins exhibiting cross-reactivity to mouse IgG.

All these interfering antibodies are capable of simulating an analyte of interest when body fluids are tested in an immunoassay. This interference can result in false positives, false negatives and all graduations in between these two extremes. There is a need in the art for methods and devices that accurately detect analytes in body fluids in the presence of interfering substances.

SUMMARY OF THE INVENTION

The present invention includes methods and devices for preventing interfering substances from affecting the accuracy of a lateral flow immunoassay. In preferred embodiments, a test strip includes a capturing zone that includes at least one mobile capturing reagent that separates at least one interfering substance from the analyte. The capturing zone is preferably located upstream of the sample application zone. In some embodiments, the reagent/conjugate zone is also located upstream of the sample application zone. The capturing zone may be located upstream of, downstream of, or overlap the reagent/conjugate zone in these embodiments.

In other preferred embodiments, one or more mobile capturing reagents are included in the elution medium/running buffer.

DETAILED DESCRIPTION OF THE INVENTION

Figure 1:
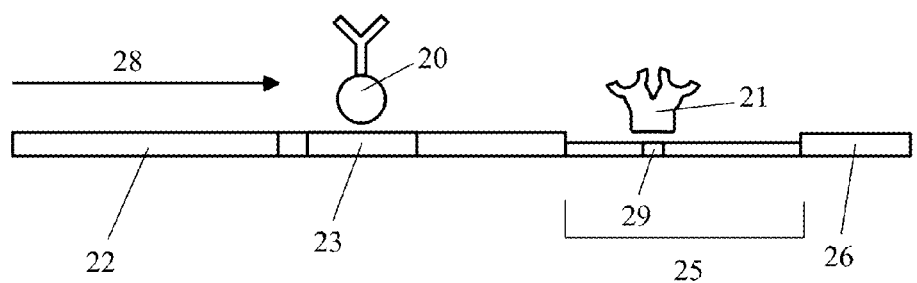
FIG. 1 schematically shows a sandwich immunoassay strip.

The present invention relates to methods and devices for detecting an analyte (also known as the target) in a sample, where the sample to be analyzed is applied to a chromatographic carrier. After separating the analyte from an interfering substance which may be present in the sample, the analyte of interest is detected on the carrier by means of an immunological assay. The invention further relates to methods and devices for reducing interference when detecting an analyte on a chromatographic carrier.

Capture of an interfering substance by one or more capturing reagents, as defined herein, occurs when the capturing reagent interacts in some manner with the interfering substance to keep the interfering substance from interfering with the detection of the analyte. Types of interactions that may occur between the capturing reagent and the interfering substance include, but are not limited to, binding, engulfing, coating, coalescing, flocculation, reacting, complexing, and adhering. If a complex results from the interaction, the complex is usually larger than the individual components. Thus, the interfering substance may be inflated, enlarged, inflamed, expanded in size or swelled when it complexes with the capturing reagent. In some preferred embodiments, the interaction is an interaction between an antibody and an antigen, thus forming an antibody-antigen complex that includes the interfering substance and the capturing reagent. The interaction between the interfering substance and the capturing reagent results in the interfering substance being captured by the capturing reagent such that it is no longer able to interfere with the reaction between the analyte and the reagents in the reagent zone and/or in the detection zone. Thus, the interfering substance no longer affects the results of the assay.

The capturing reagents may be located in a capturing zone made of materials that allow the capturing reagents to be mobile, in the elution medium, mixed and dried with the reagents, incorporated into the sample application zone, incorporated into the sample collector fleece material and/or immobilized on an immobilizing material (for example, nitrocellulose) either as a line or a zone. Any of these or combinations of these may be used depending on the test and sample matrix.

The invention provides a sensitive and rapid method for the detection of analytes, e.g. pathogens, allergy-associated components, nucleic acids, and/or low-molecular-weight compounds, in samples which may contain interfering substances. The methods and devices are suitable for diagnosis in human beings and animals, e.g. pets or livestock animals. The detection may include direct detection of the analyte and/or the detection of antibodies against the analyte, which are present in the fluid sample to be tested. Preferably, the method includes a parallel determination of a plurality of analytes. The pathogens are preferably selected from viruses or microorganisms, such as bacteria or parasites (e.g. amoebae or nematodes). The allergy-associated components are selected from allergens and anti-allergic components. The low-molecular-weight compounds may include drug molecules.

Interfering substances according to the invention include, but are not limited to, antibodies, e.g. human-anti-mouse antibodies (HAMA), or compounds exhibiting structural similarity with the analyte, e.g. low-molecular-weight compounds or nucleic acids.

The detection may include a direct detection of the target, e.g. the pathogen, and/or the detection of antibodies against the target, e.g. the pathogen which are present in the fluid sample to be tested. Preferably, the method includes a parallel determination of a plurality of targets.

More preferably, the analyte is a pathogen or a plurality of pathogens associated with conjunctivitis, an inflammation of the eye which is often caused by an infection. Most preferably, the analyte is a pathogen including, but not limited to, adenoviruses, herpesviruses, chlamydiae, cytomegaloviruses, pseudomonas, streptococci, haemophilus, staphylococci, amoebae and combinations thereof. These ocular pathogens associated with conjunctivitis replicate intracellularly. Therefore, in embodiments testing for ocular pathogens related to conjunctivitis, where there is no pretreatment of the sample prior to transfer to the sample analysis device, it is important to either use an alkaline buffer solution to rupture cellular membranes and enhance release of the antigen and/or include a lysing agent to lyse the cellular membranes in situ.

Alternatively, the analyte of interest may be a low-molecular-weight compound. In a preferred embodiment, the analyte to be detected is a drug molecule such as heroin or methamphetamine.

The invention also includes the detection of a plurality of pathogens, allergens, nucleic acids or low molecular-weight compounds on a single chromatographic carrier. The sample analysis device may allow a simultaneous detection of a plurality of low molecular-weight compounds, allergy-associated components or pathogens.

The body fluid is preferably whole blood, serum, or a fluid from a body surface selected from mucose membrane fluids (of the oral, nasal, vaginal, and ocular cavities) tears, penile fluids, secretions from glands and secretions from lesions or blisters, e.g. lesions or blisters on the skin. More preferably, the sample is selected from oral, nasal, ocular, genital and rectal fluids and secretions from skin lesions or blisters. Most preferably, the sample is an eye fluid, sweat or saliva.

In preferred embodiments, the sample is a fluid that does not drip or flow after it is collected. Instead, the fluid is a congealed mass, such that, after the sample is collected on the sample collector, the sample can be held vertically or even upside down, and the sample remains on the sample collector. For example, when an eye sample is collected and not subject to pretreatment, the sample remains on the sample collector even if held vertically or upside down, primarily due to surface tension. This is because the sample is effectively trapped and contained on the sample collector material, for example a sample collector fleece. In preferred embodiments, Polyethylene terephthalate (PET) fibers, such as Dacron® fibers, or nylon fibers are used because the binding is not specific or permanent, so these fibers "release" the analyte when wet. The phenomenon is similar to gently mopping up a spill by a paper towel such that the moisture is held in the pores and by the surface tension. Other materials that could be used for the sample collector fleece include, but are not limited to, polyesters, cellulose, rayon, calcium alginate, a microengineered mechanical structure containing microcapillaries and/or microchannels, or other fabrics and meshes. In embodiments where a sterile collector material is needed to collect a human body fluid, materials that can be sterilized and are approved for bio-compatibility are preferably used.

A significant advantage of the method is that test results are provided within the medical consultation period, e.g. in a few minutes. Preferably, the results are provided in a time period up to 20 minutes, more preferably up to 15 minutes. The test may also be run up to 24 to 48 hours after the sample has been taken from the patient. Also, as the test is noninvasive, it poses very little risk to the patient. Thus, the best available treatment can be applied on a timely basis for a specific pathogen. A further advantage over prior art methods is that only a few microliters of sample are required to perform an analysis. The sample is preferably about 0.1 µl to about 100 µl, more preferably about 0.2 µl to about 20 µl and most preferably about 0.5 µl to about 10 µl.

The invention may be performed by means of a simple test kit. Handling of the test kit does not necessitate additional laboratory equipment, further handling of reagents or instrumentation. Another important advantage of the invention described herein is that the detection limit is typically 10 to 100 times lower than currently available diagnostic tests because samples do not require dilution before they are transferred to the analysis device. Therefore the methods of the present invention are more sensitive and accurate than methods of the prior art.

In some of the embodiments of the invention, a body fluid sample is non-invasively collected with a collection device or swab member, respectively. The collection step preferably includes wiping or dabbing the swab member over a surface of the body containing body fluid to be tested. Preferably, the swab member is sterile. The swab member may be dry or pretreated with a fluid before the collection step.

In preferred embodiments, there is no pretreatment of the swab member, and the sample is collected and transferred to the sample analysis device without any treatment of the collected sample. By collecting the sample with a collection device and not subjecting the sample to pretreatment steps such as extracting and/or diluting the sample, degradation of the sample is avoided. The analyte to be tested preferably remains intact or in its native form surrounded or mixed with the other naturally occurring substances in the sample.

In the prior art, when the sample is extracted and diluted in buffer, the sample is often no longer intact. This may change the "conformation" of the analyte due to its stability or lability. By collecting a sample directly using a collection device and not pretreating the sample, the native nature of the sample is preserved in the concentrated form. Since this results in a higher concentration of sample in less volume, it increases the sensitivity of the test. In addition, with no dilution of the sample, the time of appearance and the intensity of the test line are directly proportional to the analyte concentration. Using a spectrometer, it is possible to get absolute numerical quantification. In addition, not having to pretreat the sample makes the test easier, faster, and less expensive. It also permits the test to be performed in a clinical setting, by doctors, nurses, or lab technicians. In test strips used to detect conjunctivitis, the sensitivity of the tests is comparable to the sensitivity of ultra-sensitive polymer chain reaction tests.

The prior art methods and devices required pre-treatment. Some of the reasons that it was believed that pretreatment was necessary included the mistaken belief that pretreatment would result in a more homogeneous sample. Another reason was that it was believed that concentrated samples needed to be buffered before conducting a binding assay. Others described the need to wash the sample, remove contaminating particles and substances that potentially could cause a non-specific binding reaction and therefore a false positive test result. There was also a generalized belief in the prior art that a larger homogeneous sample produced the most sensitive and specific assay test results.

On the contrary, the present invention overcomes all the prior art issues of inhomogeneous, highly concentrated or highly contaminated samples. As described by the material principle interfacial polarization, in inhomogeneous dielectric materials there are charge distributions occurring at the interfaces of the phases making up the inhomogeneous dielectric. In an "intact" (undiluted or undisturbed) in vivo infectious body fluid sample the charges or charge carriers are impeded by trapping at impurity centers or at the phase interfaces. The characteristic of this "intact" sample results in a two layer capacitor effect resulting in space-charge polarization. As the present invention has shown, the characteristic of an "intact" inhomogeneous nature results in higher binding efficiency and therefore a more sensitive assay.

It was unknown what effects body fluids, including blood, tears, and purulent exudates, would have on different collector fleece materials until the present invention. Specifically, it was unknown whether the analytes would be effectively released from the other cellular material and transferred from a sample collector to a sample analysis device.

It is particularly useful to transfer the sample without pretreatment in embodiments for diagnosing conjunctivitis. In these embodiments, the sample is preferably an eye fluid sample. Prior to the present invention, there was no method for diagnosing conjunctivitis that collected an eye fluid sample with a swab member, and then transferred the sample to a sample analysis device without pretreatment, where at least part of the eye fluid sample was released directly from the swab member to a sample application zone of the device. In the prior art, one of the reasons that those skilled in the art believed that pretreatment was necessary was because it was traditionally believed that cellular material collected with a conjunctival swab required placement in an extraction buffer to increase its release from the swab into the fluid. This perceived increased availability of analyte was thought to lead to a greater concentration and efficiency during the transfer to the test strip and thus enhanced sensitivity. In reality, placing the swab in an extraction buffer has two major limiting effects. First, it dilutes the free analyte and it does not obtain 100% efficient transfer of material from the swab to the solution.

In contrast, the direct transfer of antigen has several dramatic and unanticipated effects. The material collected is rich in cellular material and this gets transferred at a high concentration to the test strip without any dilution. Since the sample collector comes in direct contact with the test strip, it allows more efficient transfer of the material. Further, it allows for a micro-filtration process to occur that further concentrates the elutant by removing cellular debris.

In some embodiments, the sample size is preferably a few microliters. After transfer of the sample to the sample application zone (preferably without treating the sample), elution medium (also known as running buffer) is added. Prior art methods of running lateral flow immunoassays were unable to perform this washing step. For example when collecting an eye sample to test for eye infections such as conjunctivitis, the sample size is preferably 3 to 10 µl. In this example, 150 to 200 µl of elution medium is then added to the test strip. As a comparison with different assay systems, this 50 to 60 fold washing exceeds the washing performed in machine dependent ELISA tests.

In one example of collecting a sample, using a gentle swirling motion, a sterile swab member may be applied to the body surface or mucous membrane of concern and allowed to capture any pathogens, low-molecular weight compounds, and/or allergy-associated components contained in the body fluid.

The swab member may be a part which is separate from the sample analysis device. The sample is then transferred by contacting the sample analysis device with the swab member under conditions where at least a part of the sample on the swab member is transferred to the sample analysis device. In this embodiment, the swab member preferably contacts a sample application zone on the analysis device from which the sample is then transferred to the detection zone. The contact preferably includes fixing the swab member in a contact position with the sample analysis device in which the sample collection zone of the swab member is in direct contact with the sample application zone of the analysis device. Thus, the swab member and/or the analysis device preferably includes fixing means for providing a fixed contact between both parts in a predetermined position. Alternatively, the swab member may be an integrated part of the sample analysis device and the transfer includes passing at least a part of the sample on the swab member to the sample application zone on the sample analysis device.

The transfer of the sample from the swab member to the sample application zone on the sample analysis device is preferably a direct transfer, i.e. the transfer takes place without pretreatment of the sample on the swab member. In embodiments without pretreatment of the sample or the swab member, microfiltration occurs in the region where the swab member fleece directly contacts the fleece on the strip. The fibers of the fleeces interlock to form a grating or physical interference. Thus, larger elements contained in the sample are held back and not transferred to the sample analysis device. In embodiments where the reagent zone (also known as a conjugate zone) is upstream of the sample application zone, the elution medium contacts the reagent zone, thus migrating the reagent through the "filter". As the reagent moves through the sample application zone, it elutes the smaller analytes. Also, when using samples from mucosal membrane fluids, mechanical disruption of the mucous in mucosal membrane bodily fluids purifies the sample and the analyte of interest.

In other embodiments, the transfer includes an elution of the sample from the swab member with an elution medium, e.g. a buffer or water. The elution medium may be added from an external source or may be provided e.g. as a reservoir within the analysis device. Further, the transfer is preferably a chromatographic and/or capillary transfer of fluid to the detection zone on the sample analysis device.

In some preferred embodiments, the swab member is placed on a lateral flow test strip. With this step, the collected specimen is transferred directly on an immunochromatographic or enzymatic test strip. The test strip includes one or several capillary active fleeces or membranes.

The detection process will be either started directly with sample transfer or may require an elution medium to be applied for sample analysis. In some embodiments, the elution medium is simple tap water. In other embodiments, the elution medium is an alkaline buffer solution. In the case of an immunochemical test strip, the chosen elution medium moves towards a detection zone and thereby passes the contact site within the collection device. The analyte is eluted by the elution medium and carried with it to the detection zone. In the detection zone, the analyte is determined by qualitative and/or quantitative methods, e.g. in an immunological binding reaction.

The test strip can be made of one single chromatographic material, or preferably several capillary active materials made of the same or different materials and fixed on a carrier backing. These materials are in close contact with each other so as to form a transport path along which a liquid driven by capillary forces flows from the start zone, passing the contact site of the swab and the detection zone, towards a waste zone at the other end of the strip.

Some preferred materials and membranes for the test strip include, but are not limited to, Polyethylene terephthalate (PET) fibers, such as Dacron® fibers, nitrocellulose, polyester, nylon, cellulose acetate, polypropylene, glass fibers, and combinations of these materials and their backings. The characteristics of the fleeces and membranes depend upon the types of materials used for a particular region or zone of the test strip or collection device. As described herein, materials that allow reagents (including those in the reagent zone, the capturing zone, or any of the other zones or lines described herein) to be mobile and travel with the elution medium include fleece materials or fibers, where the binding is not specific or permanent, so that the analyte and reagents may be released when they encounter the elution medium or with large sample volume. Some of these materials include, but are not limited to, Polyethylene terephthalate (PET) fibers, such as Dacron® fibers, nylon fibers, polyester fibers, cellulose acetate fibers, polypropylene fibers, glass fibers, and other fabrics and meshes. In contrast, materials that immobilize reagents in a particular zone (including, for example, the reagents immobilized on the test line and control line of the detection zone and the capturing reagents in the embodiments where the capturing reagents are immobilized in a capturing zone downstream of the sample application zone) include, but are not limited to, nitrocellulose and nylon fibers chemically treated such that individual fibers in the nylon mesh bind permanently to reagents such as proteins. Some methods for manufacturing different portions of the strip include, but are not limited to, striping, spraying, soaking and drying materials onto the strip.

The test strip materials preferably filter and/or retain particulate matter as well as cell debris, the precipitates, etc. in the membranes. In addition, since the volume of the sample is preferably so small, the sample stays put in the materials and the elution buffer flowing directly underneath the sample contacts and transports the sample such that the sample may be extracted, lysed, and/or filtered before it reaches the test line of the detection zone.

Furthermore, devices and test kits of the present invention preferably perform the methods described herein.

In some preferred embodiments of the invention, it is possible to make use of different immunological testing procedures to detect bacterial or viral constituents on one or several immunological binding reactions. In a preferred embodiment, a chromatography test strip contains: a sample application zone (also known as an application zone) and a reagent zone containing at least one labeled binding partner that is able to migrate with the elution medium. The binding partner is capable of specifically binding to an analyte and to a further specific reagent in the detection zone. The detection zone contains a first section for the detection of a first analyte, e.g. a test line, including an immobilized specific binding partner for the analyte, and optionally further sections for the detections of further analytes, and at least one control section, e.g. a control line comprising an immobilized specific binding partner of an indicator substance indicating the functionality of the test kit.

In a preferred embodiment, the specific binding partners for the analytes in the reagent and the detection zone are monoclonal, polyclonal or recombinant antibodies or fragments of antibodies capable of binding to a pathogen. In other embodiments, specific binding partners may also be antigens capable of binding to antibodies against a pathogen or an allergen. Other types of binding partners are bioorganic macromolecules like aptamers or receptors, nanoparticles or nucleic acids. The methods and devices of the present invention can be used for any binding assays, and can avoid the use of antibody/antigens or nucleic acids, for example, in ligand-receptor binding assays and enzyme substrate binding assays.

The reagent zone may be located before (see FIGS. 10-11 and 13-16), within or after the sample application zone (see FIGS. 5-6, 12 and 17-20), seen in the running direction of the eluent liquid. In any of these embodiments, the reagent zone is preferably made of a material that permits the reagents in the reagent zone to be mobilized by the elution medium or by the large volume of the transferred sample itself. At least one test line is located after the reagent/application zone and at least one control line is located after the test line. Together, the test line and control line make up the detection zone. The detection zone is preferably made of a material that immobilizes the reagents on the test line and the control line.

Figure 2:
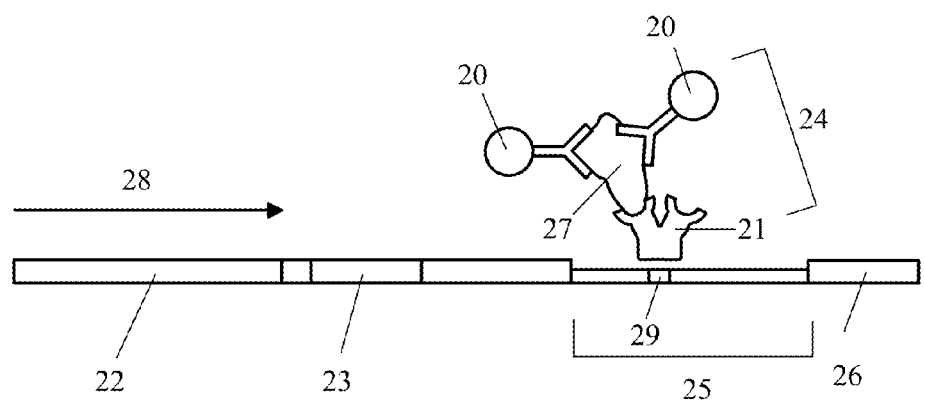
FIG. 2 shows a lateral flow immunoassay strip with an analyte sandwich-complex.

Detection of at least one analyte that has been separated from at least one interfering substance is achieved by at least one detection zone present on the carrier, the detection zone including an immobilized binding molecule specific to an analyte. The binding molecule immobilizes the labeled analyte or the labeled analyte-analogue by immune reaction in the detection zone, thus building up a visible test line in the detection zone during the immunoassay process (FIG. 2).

Depending on the type of detection method, different binding partners are present in the different zones. In a sandwich immunoassay, it is preferred to have a labeled, non-immobilized analyte binding partner in the reagent zone. The binding partner forms a complex with the analyte which is bound to the immobilized binding partner at the test line. In a preferred manner, the label of the reagent binding partner is an optically detectable label. Forming a complex in the detection zone at the test line concentrates and immobilizes the label and the test line becomes visible to the naked eye, indicating a positive test result. Particularly preferred are direct labels, and more particularly, gold labels which can be best recognized by the naked eye. Additionally, an electronically photometrical read out device can be used to obtain more precise results, including a semi-quantification of the analyte. Other labels may be latex, fluorophores or phosphorophores.

The visual label may be any label visible to the naked eye, including, but not limited to, colored particles such as colloidal gold, dyed latex beads, selenium, or carbon. In some embodiments, the visual tags are also coated with fluorescing elements. In some embodiments, the fluorescing element is a fluorescing dye. Alternatively, a mixture of preferably colorless fluorescing latex bead conjugates are mixed with colloidal gold (a visible spectrum) conjugates, or conjugates producing a visible read test line, in lateral flow immunoassays to enhance sensitivity of the assay and to aid in visually reading true positives and true negatives. In embodiments where nanoparticles are used, the nanoparticles that may be used include, but are not limited to, selenium, carbon, and colloidal gold.

In order to test ocular fluids, a sample may be collected with a sample collection device from the patient's eye by a health care professional. The sample collection device should be wiped or dabbed slightly several times in the inferior fornix of the lower eye lid. If necessary, the collection device may be wet with sterile physiological saline to decrease patient's discomfort. This procedure is well known in the ophthalmology practice, as it is necessary for collecting specimens for conventional laboratory analysis. Generally the sample collection device includes a capillary active material suitable for receiving a body fluid sample. In a preferred manner, the sample collection material is made out of fibers on the basis of cellulose, polyester, rayon or calcium alginate. However, the sample collection device can also be designed as a microengineered mechanical structure containing microcapillaries and/or microchannels.

After the sample is collected, the collection device is fixed to a plastic housing containing the test strip (see FIG. 9) and thereby the collection applicator is slightly pressed on the sample application zone of the strip. The collection device remains in this position for the test.

In an alternative embodiment, the sample is taken by a standard swab member as currently used in the physician's office or emergency rooms. This swab member is subsequently pressed into the sample application zone of the chromatographic test strip by means of an additional device similar to the sample collection unit.

In another preferred embodiment, the sample is taken by a swab member and the sample collection device is pressed for only a short time into the sample application zone of the chromatographic test strip. A short period of time preferably means a time up to 20 seconds, particularly between 0.1 and 10 seconds. A transfer of the sample from the swab to the sample application zone occurs within the contact period.

In the next step, an elution medium is applied by dipping the absorbent pad into the chromatographic liquid. The absorbent pad is made of a particularly well-absorbing material which delivers the liquid for the immunochemical or enzymatic reactions. Preferred elution media are water or buffer solutions that are conventionally used in immunoassays.

Alternatively the elution medium is contained in a reservoir which may be integrated within the analysis device, e.g. as an ampoule or a blister. The reservoir may be opened by fixing the swab member or sample collection device on the detection part of the device or by additional means. After a time period of up to 15 minutes, preferably within two to five minutes, the result can be read out in the detection zone. The result is considered positive when at least a partial area of the test line and the control line show a color change.

Figure 6:
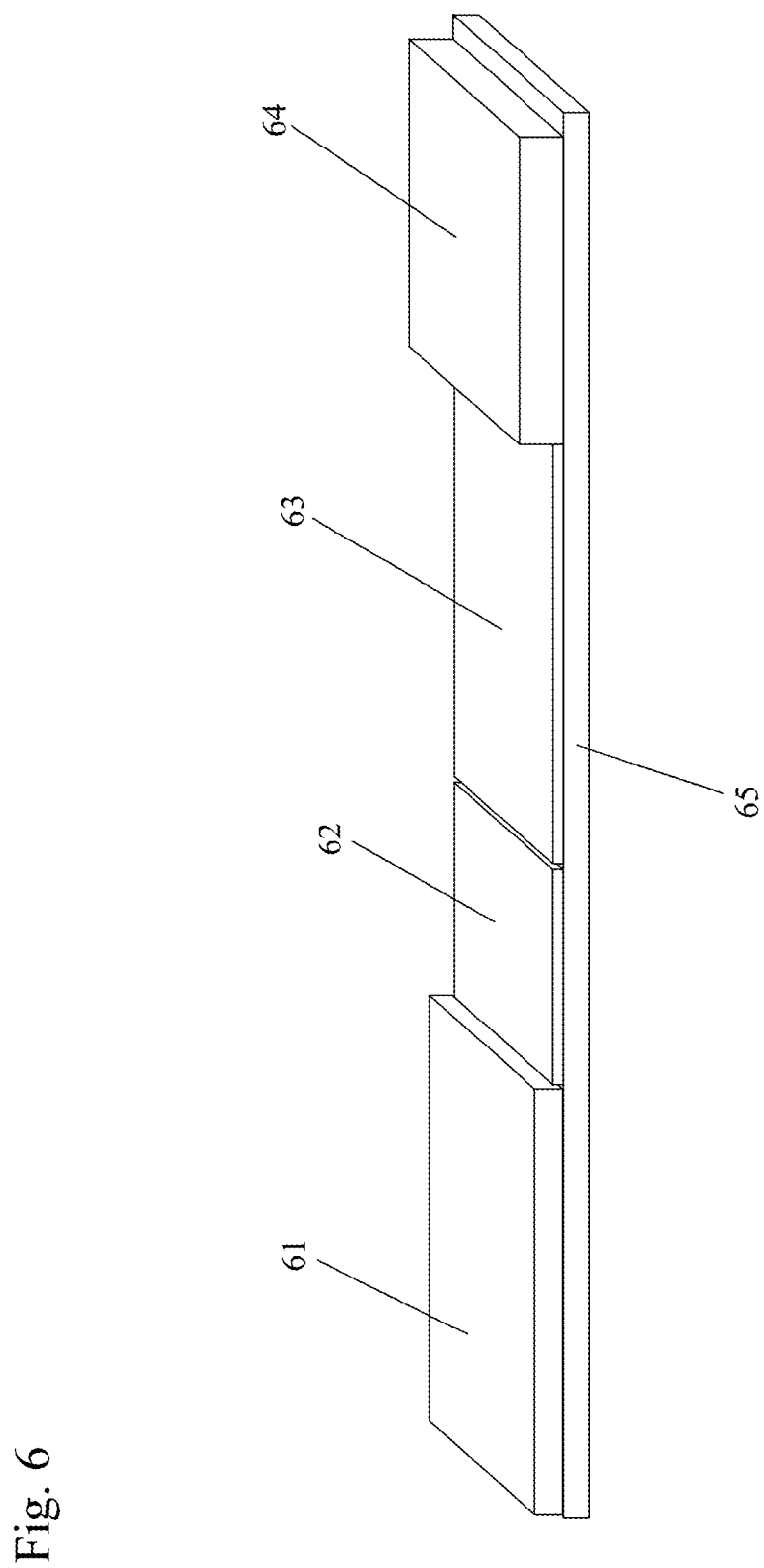
FIG. 6 shows a sample analysis device that may be used in embodiments of the present invention.
Figure 7:
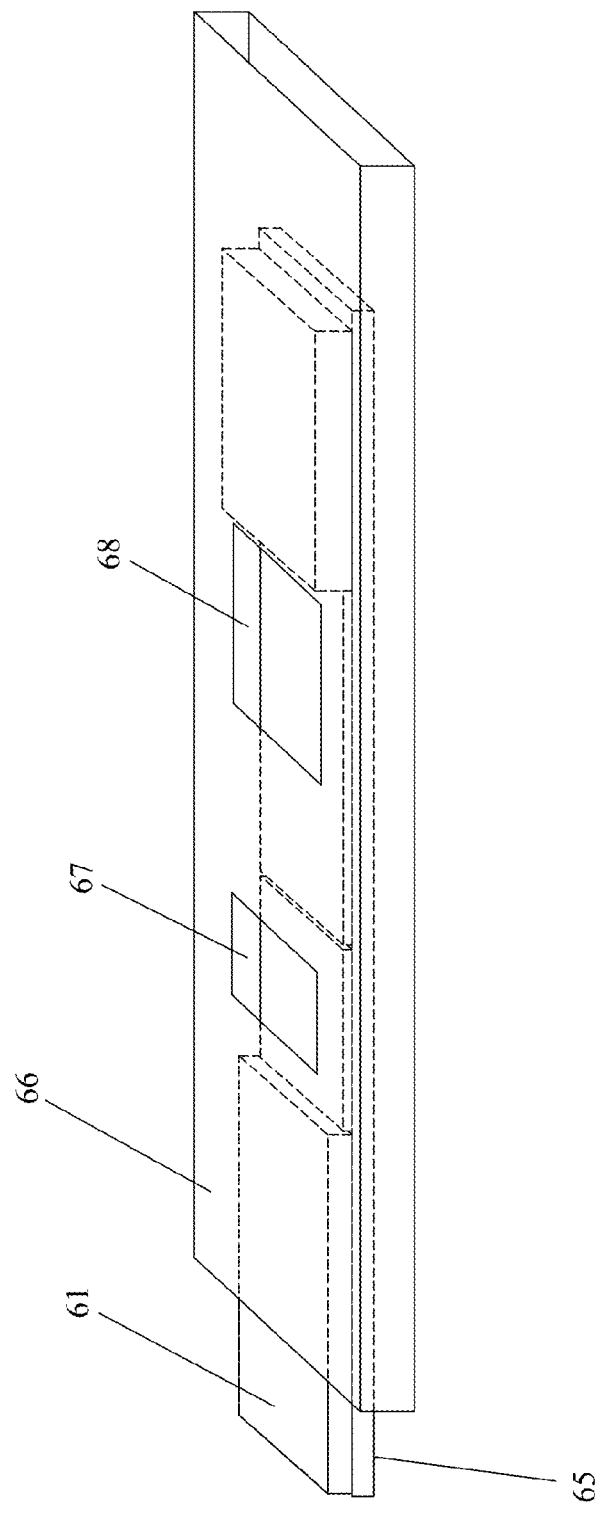
FIG. 7 shows a housing containing the strip of FIG. 6.

An example of a chromatographic test strip that may be used in the present invention is shown in FIGS. 6 through 9. The test strip in these figures preferably includes a plurality of different strip materials including, but not limited to, polyesters, glass fibers, nitrocellulose, nylon, polypropylene, Polyethylene terephthalate (PET) fibers, such as Dacron® fibers, and cellulose acetate. The device preferably includes an absorbent pad (61), a sample application zone (62), a detection zone (63), and a waste zone (64). The strip materials are arranged on an adhesive plastic backing (65). The absorbent pad (61) is provided in this example for adding an elution medium in order to facilitate the elution of the sample to the detection zone (63). FIG. 7 shows a housing (66), which is preferably plastic, containing the strip shown in FIG. 6. A sample application window (67) brings a collection device into contact with the strip. The test result is displayed in the read out window (68).

Figure 8:
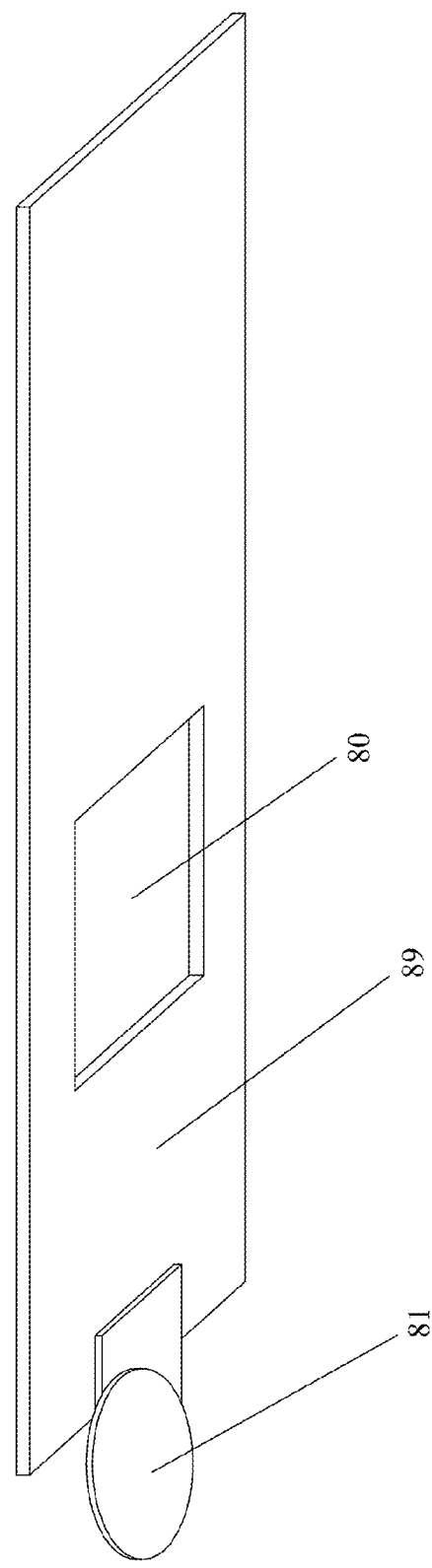
FIG. 8 shows a collection device for collecting a sample.

FIG. 8 shows an example of a collection device for collecting a sample. In one example, the collection device is a swab member. The material used for the sample collection material portion of the collection device is preferably a sample collector fleece. In a preferred embodiment, the sample collection material is made of Polyethylene terephthalate (PET) fibers, such as Dacron® fibers, which, in assays that collect bodily fluids such as eye fluid, effectively captures the body fluid and the infectious agent. In other embodiments, nylon may be used. Other materials, as described herein, could alternatively be used. The fleece holds a precise amount of fluid, so precision regarding the amount of sample being taken is the same or better than in systems that use a pipette.

In preferred embodiments, the device includes an indicator which indicates when sufficient material has been collected. For example, one could use a pH indicator such as Phenol Red, which, in a very dilute and dried state, is very light. When exposed to moisture, especially with a different pH, the color changes to red. An evenness of the red color indicates evenness of the moisture uptake. The dye permits the naked eye to see colorless liquids, for example tears, on white materials, for example Dacron® fibers, which would otherwise be very difficult to see with the naked eye. Other dye indicators may be used depending upon the application. The choice of dye indicator (and/or its pH) may depend upon the acidity/alkalinity of the body fluid being tested. For example, if the device is being used to test for sexually transmitted diseases, the fluid may be very acidic.

The collection device preferably includes a body (89), which is preferably plastic, with a sample collection material (81) fixed on it and an opening (80) corresponding to a read out window when the collection device is operatively in contact with a test strip. The collection device in FIG. 8 could be used in combination with any of the embodiments of the present invention. Similarly, transfer of the sample from the collection device to the sample analysis device without pretreatment of the sample may also be used in combination with any of the embodiments of the present invention.

Figure 9:
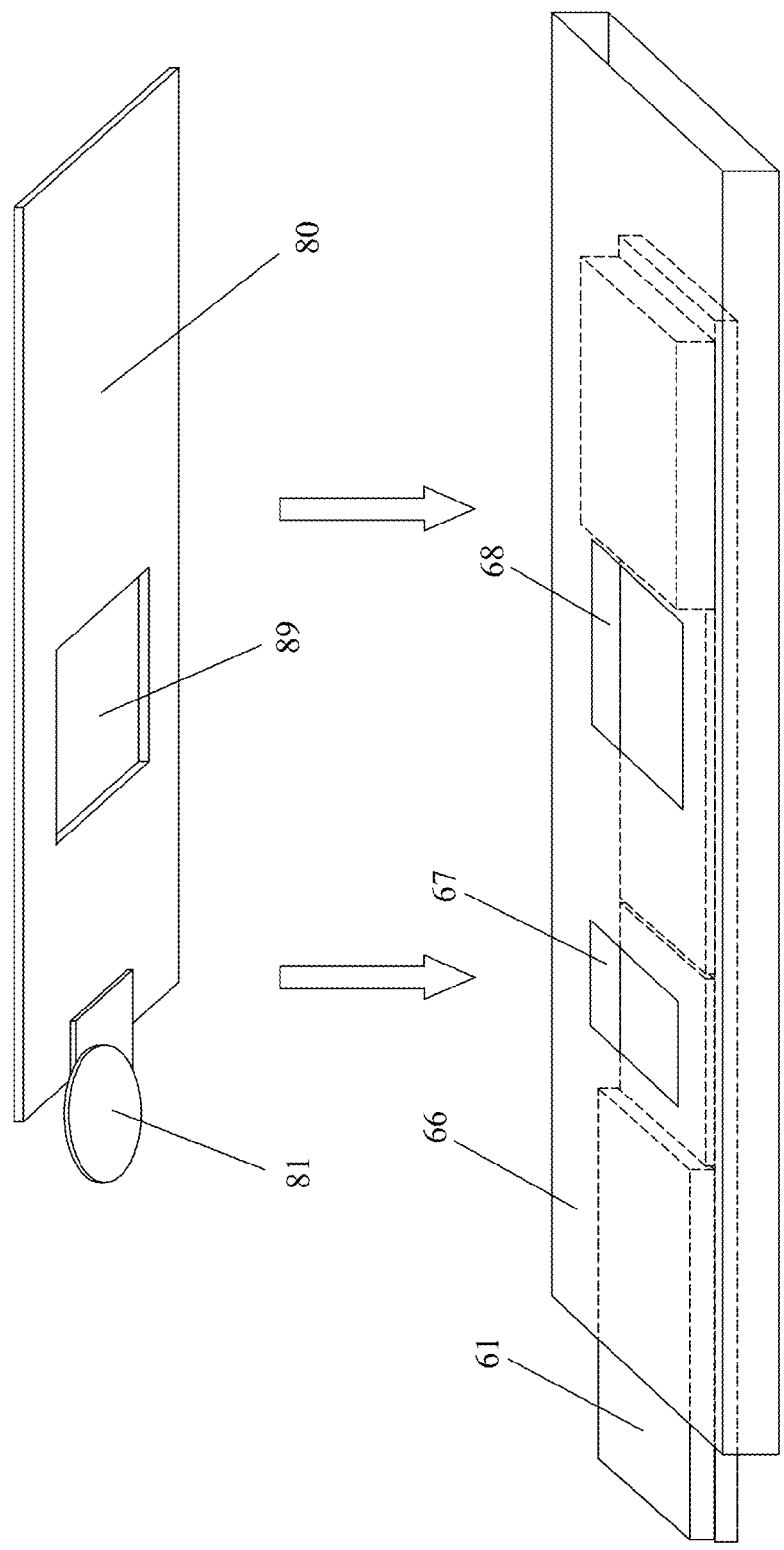
FIG. 9 shows a test kit including the sample analysis device of FIGS. 6 and 7 and the collection device of FIG. 8.

FIG. 9 shows a test kit, which includes the sample analysis device of FIGS. 6 and 7 and the collection device of FIG. 8.

The methods and devices of the present invention preferably incorporate a capturing zone on the test strip or the sample collection device that includes at least one reagent that interacts with interfering substances in order to separate interfering substances from the analyte and reduce the occurrence of false positives or false negatives. In other embodiments, the reagents that interact with the interfering substances are part of the elution medium on a lateral flow immunoassay test strip, such as those shown in FIGS. 6 through 9, or other lateral flow immunoassay devices known in the art.

In some preferred embodiments, the capturing zone is located on a material on the test strip chosen such that the capturing reagent becomes mobile when it encounters the elution medium or large volumes of the transferred sample itself Some examples of these materials include, but are not limited to, Polyethylene terephthalate (PET) fibers, such as Dacron® fibers, nylon fibers, polyester fibers, cellulose acetate fibers, polypropylene fibers, glass fibers, and other fabrics and meshes. Preferably, the capturing zone is located separate from the test strip on the collection device, or upstream of the sample application zone on the test strip, in these embodiments.

In other embodiments, the capturing zone is located on a material on the test strip chosen such that the capturing reagents are immobilized on the test strip, and effectively act as a filter. One preferred material for the capturing zone in these embodiments is nitrocellulose. Other preferred materials include nylon fibers chemically treated such that individual fibers in the nylon mesh bind permanently to reagents such as proteins. Preferably, the capturing zone is located downstream of the sample application zone in these embodiments.

In preferred embodiments of the present invention, the interfering substance is separated from the analyte of interest. Preferably, the capturing step includes an immune reaction. In particular, the immune reaction may include immobilizing the interfering substance with an immobilized capturing reagent specific to the interfering substance. In other embodiments, the immune reaction or complex formation may include binding the interfering substance to a mobile capturing reagent specific to the interfering substance.

The interfering substance may be an antibody which interferes with the detection of the analyte, e.g. by reacting with detection reagents. For example, the antibody may be selected from human anti-mouse antibodies (HAMA), heterophilic antibodies, rheumatoid factors (RF) or any combination thereof In an especially preferred embodiment, the interfering compound is a human anti-mouse antibody (HAMA). Interfering antibodies may be separated from the sample by reaction with a capturing reagent which specifically recognizes the interfering antibody, but does not react with the analyte or the detection reagent. For example, a human-anti mouse antibody (HAMA) may be separated from the analyte by an immune reaction with a monoclonal or a polyclonal mouse antibody.

In alternative embodiments, the interfering substance may be a low-molecular-weight compound, e.g. a drug molecule, exhibiting structural similarity with the analyte. Especially preferred interfering substances are legal drugs like morphine, codeine or dihydrocodeine, all of which show high structural similarity with the illegal drug heroin and its metabolite 6-monoacetylmorphine. 6-monoacetylmorphine is measured with laboratory based instrumental methods to differentiate between legal and illegal use of opiates. Other preferred low-molecular-weight interfering substances according to the invention include, but are not limited to, amphetamine, Ecstasy or ephedrines, which exhibit interfering properties when analyzed in combination with the differently classified drug methamphetamine. Amphetamines or ephedrines are subcompounds in medications whereas methamphetamine is a classified illegal drug. Interfering drug analogues may be separated from the sample by reaction with a capturing reagent which specifically recognizes the interfering drug analogue, but does not react with the target analyte or the detection reagent.

In embodiments where one or more nucleic acids are the target analyte, DNA is a cross-contaminant for RNA and RNA is a cross-contaminant for DNA. Therefore, other nucleic acids can interfere with detecting the nucleic acid analyte of interest. Interfering nucleic acids may be separated from the sample using capturing reagents which specifically bind to the interfering nucleic acid, but do not react with the target analyte or the detection reagent.

In methods of the invention, the sample to be analyzed for the analyte of interest is applied to a chromatographic carrier. The carrier can be made of one single chromatographic material, or preferably several capillary active materials made of the same or different materials and fixed on a carrier backing. These materials are in close contact with each other so as to form a transport path along which a liquid driven by capillary forces passes a sample application zone, a reagent zone and at least one capturing zone, towards one or more detection zones and optionally a waste zone at the other end of the carrier. In an especially preferred embodiment, the carrier is a chromatographic test strip.

Preferably, the sample is directly applied to the carrier by dipping the carrier's application zone into the sample. Alternatively, application of the sample to the carrier may be carried out by collecting the sample with a dry or wetted wiping element from which the sample can be transferred, with or without pretreatment, to the carrier's application zone. In some embodiments, the wiping element is sterile and may be dry or pretreated with a fluid before the collection step. Materials suitable for wiping elements according to the invention may include synthetic materials, woven fabrics or fibrous webs. Some examples of such wiping elements include, but are not limited to, those described in German Patents DE 44 39 429 and DE 196 22 503, which are hereby incorporated by reference.

Depending on the type of detection method, different reagents are present in the carrier's reagent zone, which may be located between the sample application zone and the detection zone. In other embodiments, the reagent zone is located upstream of the sample application zone. In a sandwich immunoassay, it is preferred to have a labeled, non-immobilized reagent specific to the analyte in the reagent zone. The reagent forms a complex with the analyte which is eventually bound to an immobilized analyte binding partner at a test line in the detection zone. In a competitive immunoassay, the reagent zone preferably contains a labeled, non-immobilized analyte analogue which competes with the analyte for the immobilized analyte binding partner in the detection zone. The analyte binding partners in the reagent zone and in the detection zone are preferably monoclonal, polyclonal or recombinant antibodies or fragments of antibodies capable of binding to a pathogen or a low-molecular-weight compound. In other embodiments, the reagents may also be antigens capable of binding to antibodies against a pathogen or a low-molecular-weight compound. Other types of binding partners are biological compounds like receptors or RNA- or DNA-macromolecules or synthetic bioorganic macromolecules such as aptamers or artificial receptors, or nanoparticles.

FIG. 1 shows an example of a sandwich immunoassay strip. These devices are typically used for the detection of microbial antigens in serum and other body fluids or pregnancy testing. The immunoassay strip includes a sample application zone (22), a reagent zone (23), a detection zone (25) including a test line (29), and a waste zone (26). A control line (not shown in FIG. 1) is also preferably present. Flow (28) occurs in the direction of the arrow. Labelled antibody (20) is located in the reagent zone (23). Test line antibody (21) is located on the test line (29). Both the labeled antibody (20) and the test line antibody (21) are specific to the analyte (27) and may be mouse anti target antibodies. This figure shows a specific embodiment of an immunoassay strip design.

FIG. 2 shows a lateral flow immunoassay strip with an analyte sandwich-complex (24). The sample fluid is flowing over the strip and the analyte (27) is "sandwiched" between a labeled, non-immobilized antibody (20) and an immobilized test line antibody (21).

Figure 3:
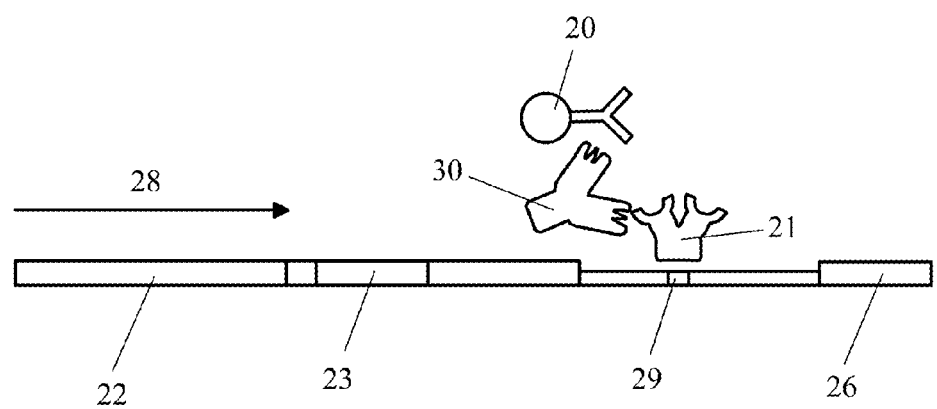
FIG. 3 shows how the presence of human anti-mouse antibodies (HAMA) leads to a positive signal in the absence of the analyte.

FIG. 3 shows how the presence of an interfering substance (30), human anti-mouse antibodies (HAMA) in this figure, leads to a positive signal in the absence of the analyte (27). This occurs as a result of bridging the soluble (20) and the immobilized analyte specific antibody (21). HAMA antibodies utilize mouse-specific epitopes on the soluble, labeled antibody (20) and the immobilized antibody (21), respectively.

Figure 4:
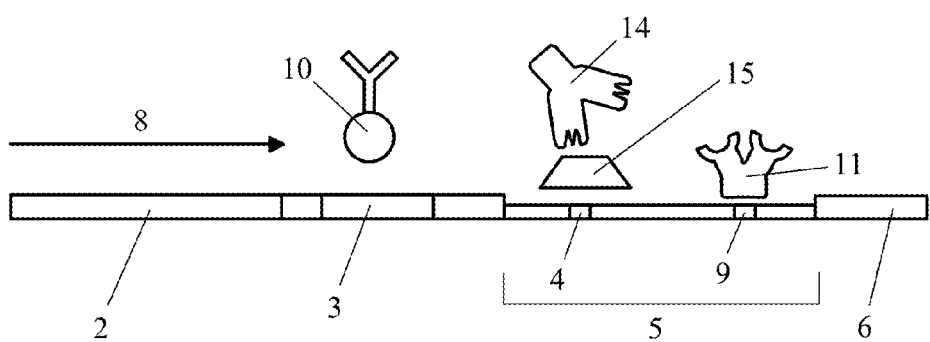
FIG. 4 shows an immunoassay strip including a capturing zone in an embodiment of the present invention.

FIG. 4 shows a lateral flow immunoassay strip with a capturing zone (4) in an embodiment of the present invention. The immunoassay strip includes a sample application zone (2), a reagent zone (3) including a mobile labeled antibody (10) specific to the analyte, a capturing zone (4) including an immobile capturing agent (15) that captures interfering substances (14), a detection zone (5) including a test line (9) with an immobile test line antibody (11) specific to the analyte, and a waste zone (6). Flow (8) occurs in the direction of the arrow. Both the labeled antibody (10) and the test line antibody (11) are specific to the analyte and may be mouse anti target antibodies. The capturing zone (4) removes the interfering antibody, HAMA in the figure, from the sample before the sample reaches the detection zone (5), thus avoiding false positive results.

In embodiments where the interfering substance of interest is HAMA, the capturing zone (4) is preferably normal mouse Immunoglobulins immobilized in the capturing zone (4), preferably on a nitrocellulose membrane.

The capturing zone (4) in these embodiments ties up human anti-mouse antibody. This is important when the visual (colloidal gold or dyed latex beads) labels are coated with specific mouse monoclonal antibody to which the human anti-mouse antibody will bind. Since the antibody has two binding sites, the human anti-mouse antibody can potentially bind to the visual reagent as well as to the immobilized reagent at the test line, which is also a mouse monoclonal antibody, potentially giving rise to a false positive. In addition, there are non-specific reactions where "sticky" substances like Rheumatoid factors and other immune complexes just stick non-specifically to proteins. By incorporating mouse Immunoglobulins upstream of the test line, these interfering substances are also effectively removed before they reach the test line. Alternatively, it may be possible to force the sticky complexes to stick to mouse Immunoglobulins in the mobile state and take away their stickiness so that these complexes just flow past the test line and do not adhere to it. For this reason, lateral flow immunoassay buffers often have Bovine Serum Albumin to "block" these unwanted phenomena. It is also possible to achieve this by varying the salt concentration, detergents or pH of the elution medium. Any or all of these strategies may be used to decrease non-specific interference.

Figure 5:
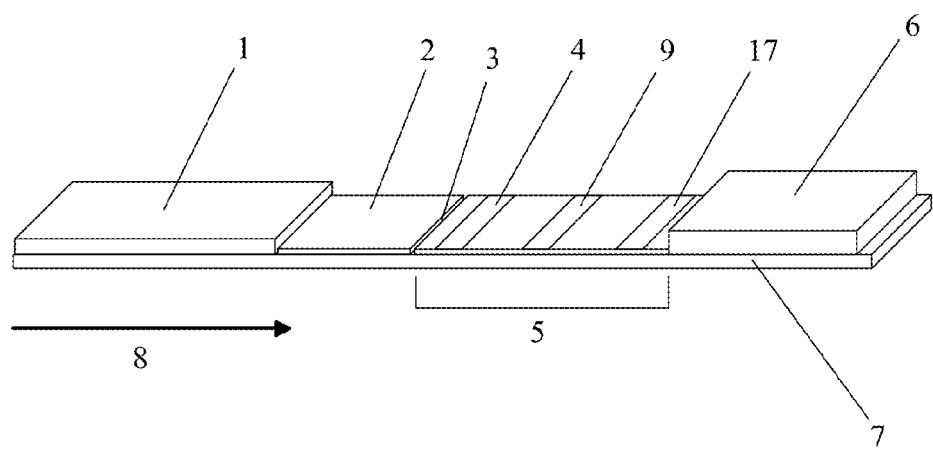
FIG. 5 shows a sample analysis device in the form of a chromatographic test strip in an embodiment of the present invention.

FIG. 5 shows one example of a sample analysis device in the form of a chromatographic test strip in an embodiment of the present invention. The chromatographic test strip in this figure preferably includes a plurality of different strip materials building an absorbent pad (1), a sample application zone (2), a reagent zone (3), a capturing zone (4), a detection zone (5) and a waste zone (6). The strip materials are preferably arranged on an adhesive plastic backing (7). The absorbent pad (1) provides a location for adding an elution medium and facilitates the transfer of the sample to the detection zone (5), which includes one or more test lines (9) and preferably at least one control line (17). Any material capable of receiving elution medium and transferring that medium in the direction (8) of fluid flow could be used, and it is not necessary to use an absorbent pad (1) made of a different material than the other sections of the test strip. The reagent zone (3) of the chromatographic test strip includes a non-immobilized reagent specific to the analyte, whereas the test line (9) of the detection zone (5) includes an immobilized reagent specific to the analyte. The waste zone (6) is also an optional section of the test strip.

In some preferred embodiments, the capturing zone (4) is a relatively large area, not just a single line of immobilized capturing reagent. In one preferred embodiment, the capturing zone (4) is approximately 1 to 4 mm wide, approximately equivalent to the width of three test lines. Using a zone instead of just one individual test line creates more area for the interfering substance to traverse and the zone permits more efficient capture of the interfering substance. In this zone, in addition to specific binding between the targeted interfering substance and the capturing reagent, non-specific binding occurs, removing other potentially interfering substances. These substances are absorbed upstream of the detection zone, and the capturing zone thus acts like a filter zone. The relatively large amount of area permits nonspecific binding of substances that would otherwise interfere with the accuracy of the test. This binding may be due to cross-reactions, specific binding, or just adherence or "stickiness" causing non specific binding. For example, the capturing zone may filter out RF and immune complexes, which are generally adherent.

In other embodiments, when the eluent (running buffer) reaches the capturing zone, which is preferably made of nitrocellulose or another immobilizing material in embodiments where it is downstream of the sample application zone, one or more capturing reagents that would interact with the interfering substance in the sample is manually added, for example as a drop, onto the test strip. The added capturing reagent interacts with the interfering substance in the sample to render it unable to bind to the test line where the analyte will become immobile. This embodiment requires the end user to add the capturing reagents to the test strip at the correct time. In kits utilizing this embodiment, the capturing reagent would need to be separately provided as a component of the kit.

In an example of the invention shown in FIG. 5, the chromatographic test strip is designed to reduce or eliminate the effects of HAMA on the accuracy of the test. In the capturing zone (4) of the chromatographic test strip, a human anti-mouse antibody (HAMA) capturing reagent is immobilized. After applying a patient sample to the sample application zone (2), the sample and the non-immobilized reagent for detecting the analyte pass the capturing zone (4) during the elution process. Human anti-mouse antibodies (HAMA) possibly present in the patient samples will be captured in this zone in order to prevent false positive signals within the detection zone (5) of the test strip resulting from nonspecific binding of HAMA to the detection antibodies.

The effectiveness in preventing false positive signals due to human anti-mouse antibodies (HAMA) in patient samples was demonstrated by applying 5 µl HAMA-positive human blood plasma to a chromatographic test strip like the one shown in FIG. 5. Three different plasma samples with concentrations of 100 ng/ml, 1494 ng/ml and 161 ng/ml of HAMA were used. In the capturing zone (4) of the test strip, purified non specific murine IgG was immobilized, which was applied at a concentration of 3 mg/ml and a dispensing rate of 0.3 µl/mm. The test strip was designed for detecting virus antigen in human body fluids using monoclonal mouse antibodies both as a capturing reagent in the capturing zone (4) and as an immobilized detection antibody in the detection zone (5). Gold-labeled monoclonal mouse antibodies were used as the non-immobilized detection reagent located in the reagent zone.

Performing a comparative test on a chromatographic test strip not including a capturing zone (4) and applying HAMA-positive plasma to the strip led to clearly false positive signals within the detection zone (5). When performing a test on a test strip including the capturing zone (4), binding of the non-immobilized gold-labeled antibodies to the capturing zone (4) due to formation of a complex with human anti-mouse antibodies (HAMA) was observed. However, no false positive signals were detected. In addition, no influence on true positive signals could be observed when confirmed virus-positive samples were tested.

In embodiments of the present invention, the sample application zone and the reagent zone may be arranged in a different way, e.g. the sample application zone may be positioned downstream of the reagent zone and/or reagents may be mobilized by the chromatographic fluid.

Figure 10:
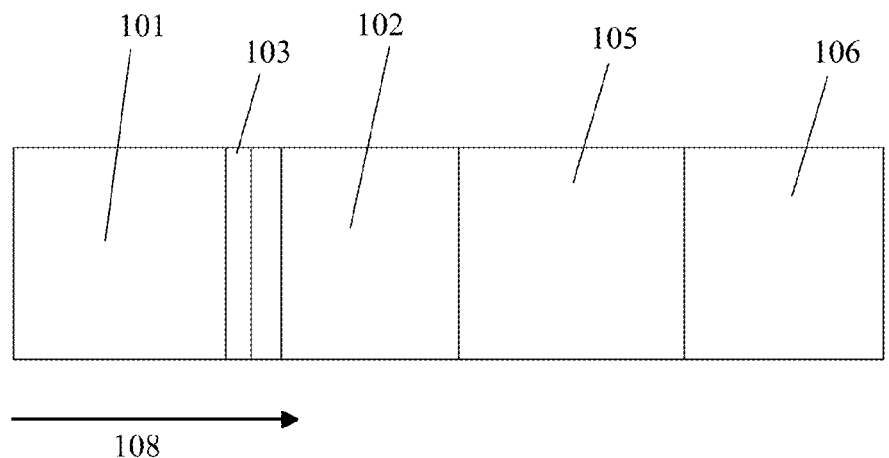
FIG. 10 shows a sample analysis device including a reagent zone upstream of a sample application zone in an embodiment of the present invention.

FIG. 10 shows a reagent zone (103) upstream of a sample application zone (102) in an embodiment of the present invention. In this embodiment, the mobile labeled reagent travels from the reagent zone (103) through the sample application zone (102), where it binds to the analyte, if present. One or more test lines in the detection zone (105) include an immobile test line reagent that also binds to the analyte, if present. There is also optionally an absorbent pad (101) upstream of the other elements, and a waste zone (106) downstream of all of the zones in this figure. Flow (108) occurs in the direction of the arrow.

Placing the reagent zone upstream of the sample application zone increases sensitivity of the assay. Some reasons for this include that there is a slightly longer "interaction" time between the reagents and the sample before their complex (half of the "sandwich") gets captured at the test line to form the full sandwich and the reagents steadily hit the concentrated sample as the flow mobilizes the dried reagents slowly and steadily. This effect is in addition to the previously mentioned higher affinity of the intact sample.

Figure 11:
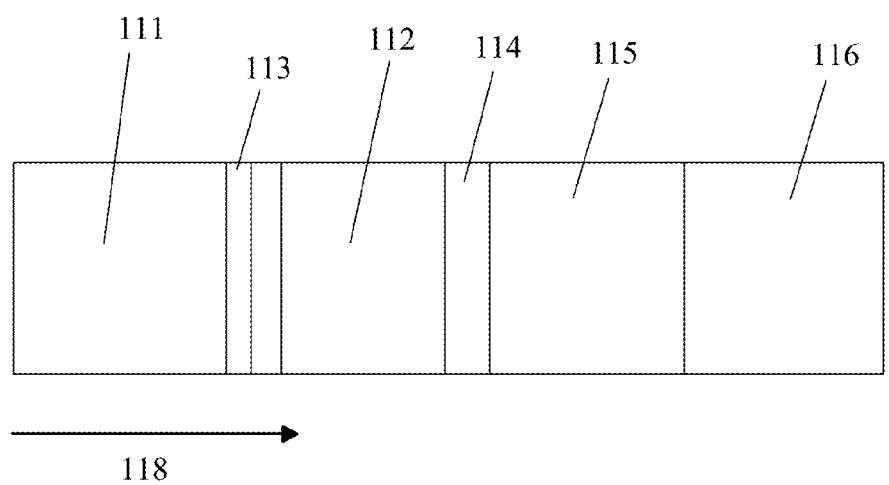
FIG. 11 shows a top view of a sample analysis device including a reagent zone upstream of a sample application zone and a capturing zone downstream of the sample application zone in another embodiment of the present invention.

FIG. 11 shows a reagent zone (113) upstream of the sample application zone (112) and a capturing zone (114) downstream of the sample application zone (112) in an embodiment of the present invention. In this embodiment, the mobile labeled reagent travels from the reagent zone (113) through the sample application zone (112), where it binds to the analyte, if present. The sample then travels to the capturing zone (114), where interfering substances interact with one or more immobilized capturing reagents. One or more test lines in the detection zone (115) include an immobile test line reagent that also binds to the analyte, if present. The presence of the capturing reagent(s) in the capturing zone (114) eliminates interference by interfering substances, such as HAMA. There is also optionally an absorbent pad (111) upstream of the other elements, and a waste zone (116) downstream of all of the zones in this figure. Flow (118) occurs in the direction of the arrow.

In other preferred embodiments, the capturing zone is located upstream of the sample application zone on the test strip. In these embodiments, one or more mobile capturing reagents in the capturing zone travel to the sample application zone, where they interact with one or more interfering substances, keeping the interfering substances from affecting the accuracy of or otherwise interfering with the assay. In these embodiments, the capturing reagent travels to the sample rather than the sample (including the interfering substance) traveling to the capturing reagent.

When the capturing zone is located upstream of the sample application zone, the elution medium mobilizes one or more capturing reagents and releases them slowly and steadily into the sample. In preferred embodiments, the sample is concentrated, for example because it has not been subject to pretreatment. Since many interfering substances in the sample are larger in size than the analyte, they move more slowly than the capturing reagent. Placing the capturing zone upstream of the sample application zone avoids any problems with the capturing reagent being washed away by the elution medium before it encounters a slower moving interfering substance.

Figure 12:
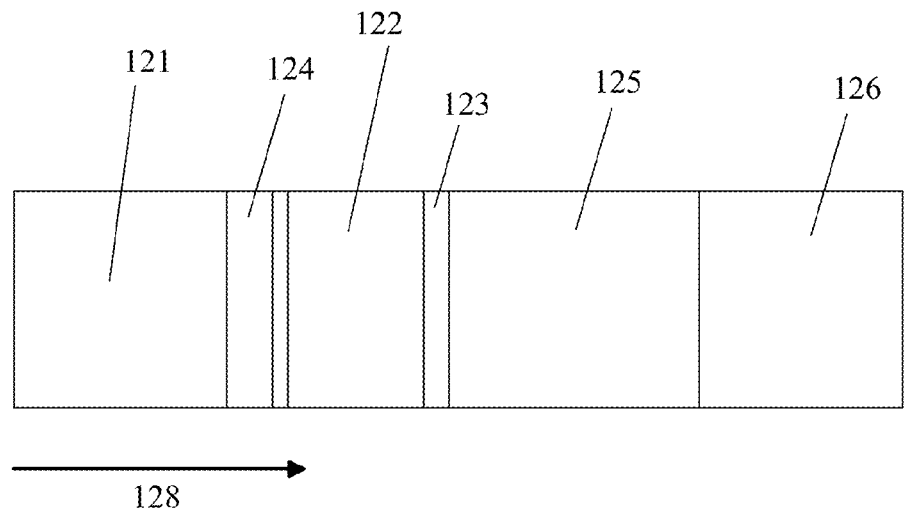
FIG. 12 shows a top view of a sample analysis device including a capturing zone upstream of a sample application zone, with a reagent zone downstream of the sample application zone in another embodiment of the present invention.

FIG. 12 shows a capturing zone (124) upstream of the sample application zone (122), with the reagent zone (123) downstream of the sample application zone (122). One or more test lines in the detection zone (125) include a test line reagent that also binds to the analyte, if present. In a preferred embodiment of FIG. 12, mouse immunoglobulins are added to the capturing zone (124) upstream of the sample application zone (122). The mouse immunoglobulins interact with HAMA, and keep it from affecting the accuracy of the test. There is also optionally an absorbent pad (121) upstream of the other elements, and a waste zone (126) downstream of all of the zones in this figure. Flow (128) occurs in the direction of the arrow.

Figure 13:
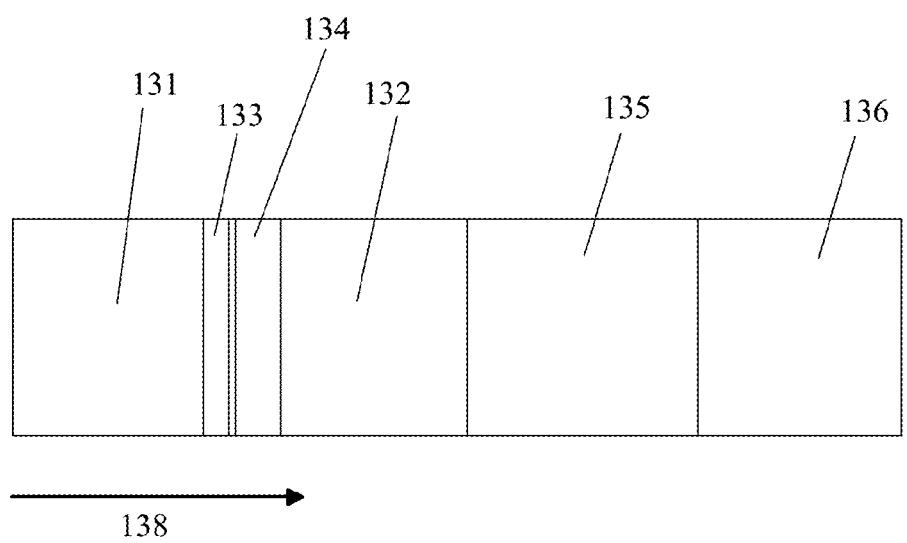
FIG. 13 shows a top view of a sample analysis device including a reagent zone upstream of a sample application zone, with a capturing zone downstream of the reagent zone but upstream of the sample application zone in another embodiment of the present invention.

FIG. 13 shows a reagent zone (133) upstream of the sample application zone (132), with a capturing zone (134) downstream of the reagent zone (133) but upstream of the sample application zone (132). One or more test lines in the detection zone (135) include a test line reagent that also binds to the analyte, if present. In a preferred embodiment of FIG. 13, mouse immunoglobulins are added to the capturing zone (134) upstream of the sample application zone (132). The mouse immunoglobulins interact with HAMA, and keep it from affecting the accuracy of the test. There is also optionally an absorbent pad (131) upstream of the other elements, and a waste zone (136) downstream of all of the zones in this figure. Flow (138) occurs in the direction of the arrow.

Figure 14:
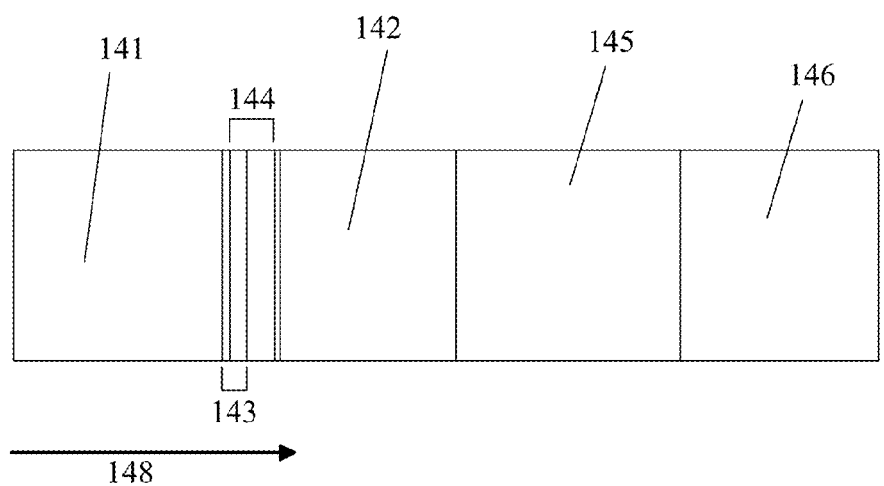
FIG. 14 shows a top view of a sample analysis device including a reagent zone overlapping a capturing zone, where both the reagent zone and capturing zone are upstream of a sample application zone in another embodiment of the present invention.

FIG. 14 shows a reagent zone (143) overlapping a capturing zone (144), where both the reagent zone (143) and capturing zone (144) are upstream of the sample application zone (142). One or more test lines in the detection zone (145) include a test line reagent that also binds to the analyte, if present. There is also optionally an absorbent pad (141) upstream of the other elements, and a waste zone (146) downstream of all of the zones in this figure. Flow (148) occurs in the direction of the arrow. While the reagent zone (143) and the capturing zone (144) only partially overlap and part of the reagent zone (143) is upstream of part of the capturing zone (144) in this figure, other overlapping configurations are possible. For example, the reagent zone (143) and the capturing zone (144) may completely overlap, with the reagents and the capturing reagent both occupying the same location on the test strip. Alternatively, a part of the reagent zone (143) may be downstream of part of the capturing zone (144). In a preferred embodiment of FIG. 14, mouse immunoglobulins are added to the reagent zone/capturing zone upstream of the sample application zone. The mouse immunoglobulins interact with HAMA, and keep it from affecting the accuracy of the test.

Figure 15:
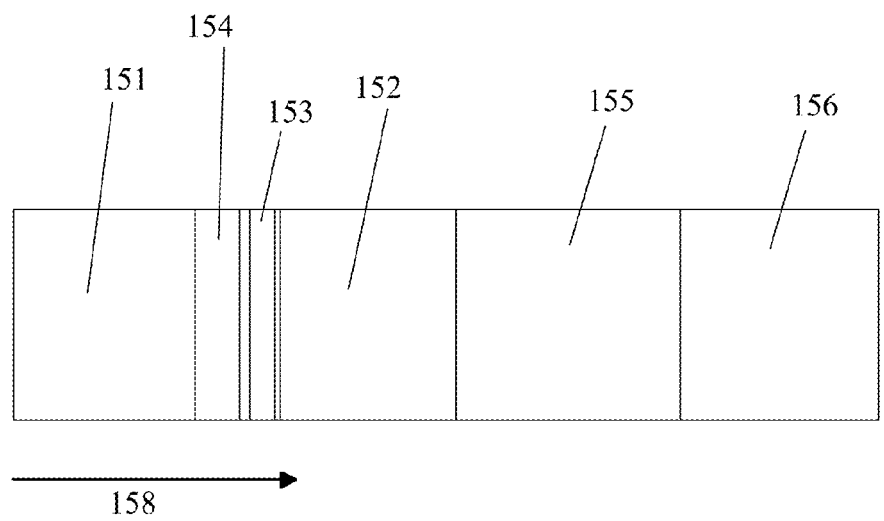
FIG. 15 shows a top view of a sample analysis device including a reagent zone upstream of a sample application zone, with a capturing zone upstream of the reagent zone in another embodiment of the present invention.

FIG. 15 shows a reagent zone (153) upstream of the sample application zone (152), with a capturing zone (154) upstream of the reagent zone (153). One or more test lines in the detection zone (155) include a test line reagent that also binds to the analyte, if present. There is also optionally an absorbent pad (151) upstream of the other elements, and a waste zone (156) downstream of all of the zones in this figure. Flow (158) occurs in the direction of the arrow. In a preferred embodiment of FIG. 15, mouse immunoglobulins are added to the capturing zone (154) upstream of the sample application zone (152). The mouse immunoglobulins interact with HAMA, and keep it from affecting the accuracy of the test.

Figure 16:
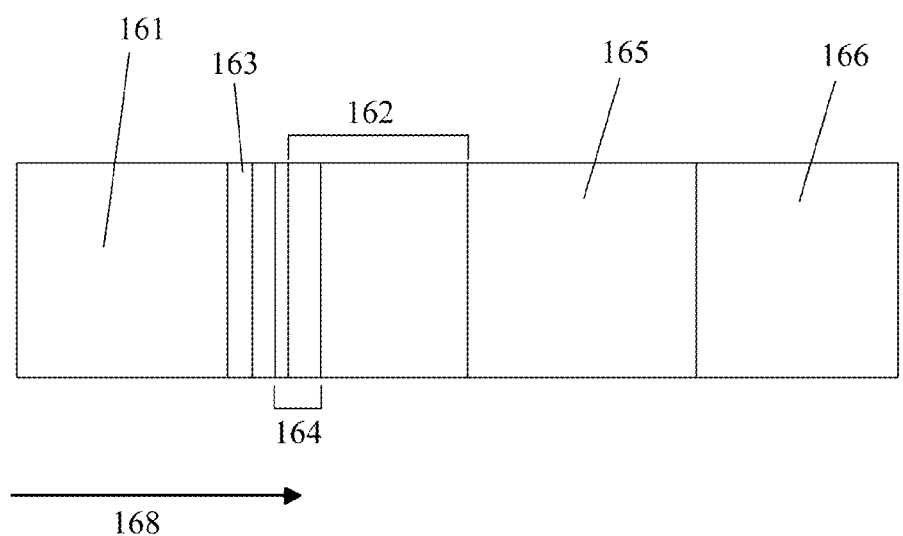
FIG. 16 shows a top view of a sample analysis device including a reagent zone upstream of the sample application zone, and a capturing zone overlapping the sample application zone in another embodiment of the present invention.
Figure 17:
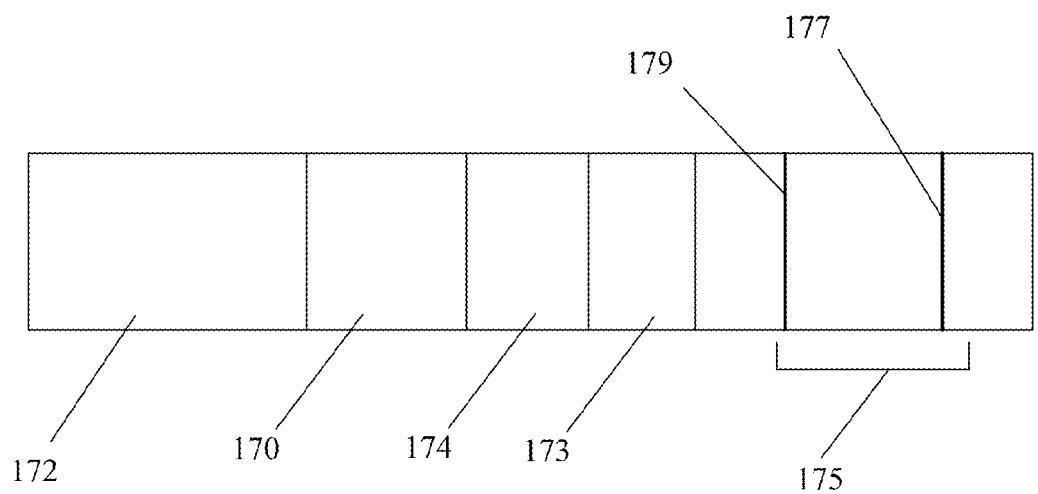
FIG. 17 shows a sample analysis device including a capturing zone between a sample application zone and a reagent zone in an embodiment of the present invention.
Figure 18:
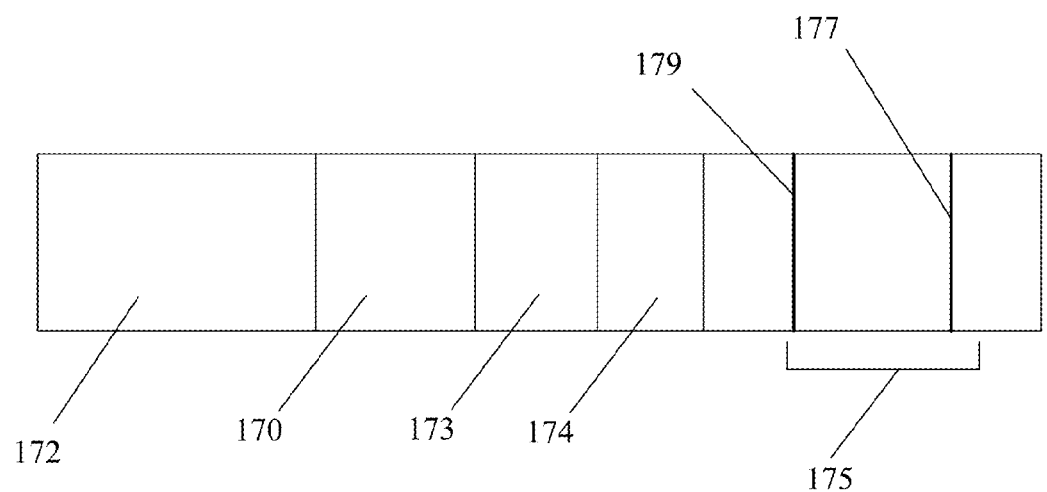
FIG. 18 shows a sample analysis device including a capturing zone between a sample application zone and a detection zone in another embodiment of the present invention.
Figure 19:
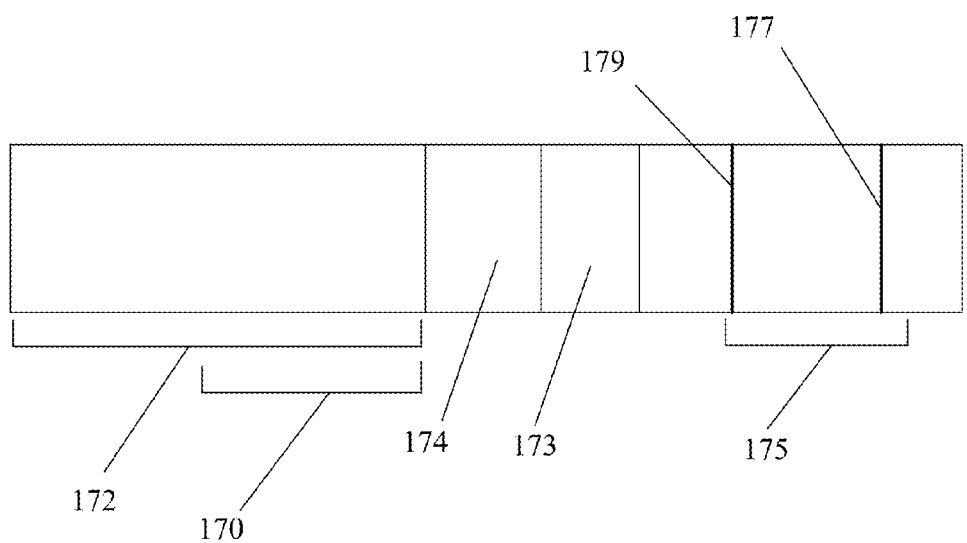
FIG. 19 shows a sample analysis device including a capturing zone between a sample application zone and a reagent zone in another embodiment of the present invention.
Figure 20:
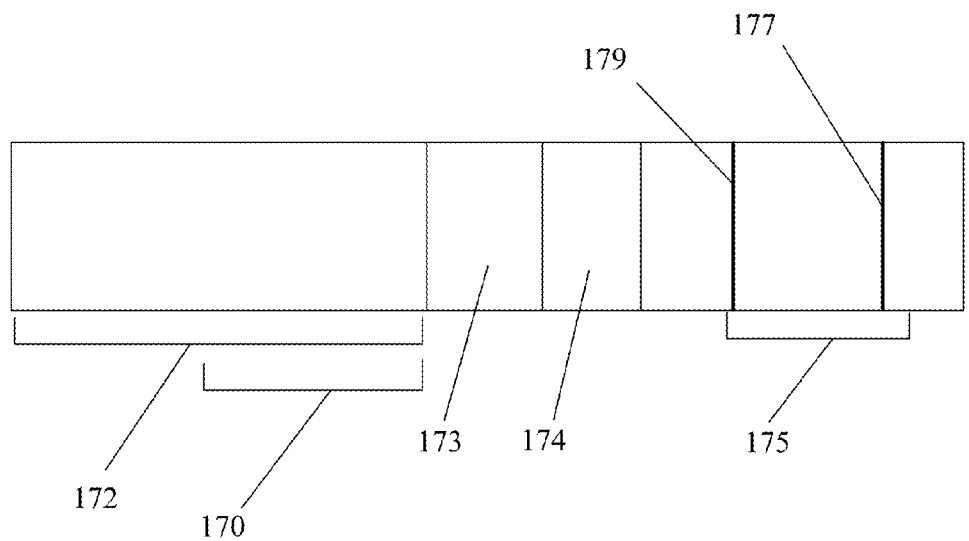
FIG. 20 shows a sample analysis device including a capturing zone between a sample application zone and a detection zone in another embodiment of the present invention.

FIG. 16 shows a reagent zone (163) upstream of the sample application zone (162), and a capturing zone (164) overlapping the sample application zone (162) in an embodiment of the present invention. One or more test lines in the detection zone (165) include a test line reagent that also binds to the analyte, if present. There is also optionally an absorbent pad (161) upstream of the other elements, and a waste zone (166) downstream of all of the zones in this figure. Flow (168) occurs in the direction of the arrow. While the sample application zone (162) and the capturing zone (164) only partially overlap and part of the sample application zone (162) is downstream of part of the capturing zone (164) in this figure, other overlapping configurations are possible. For example, the sample application zone (162) and the capturing zone (164) may completely overlap, with the sample being applied directly on top of the capturing reagent. In this embodiment, the capturing reagent may be mobile or immobilized on the test strip. Alternatively, a part of the sample application zone (162) may be upstream of part of the capturing zone (164). In a preferred embodiment of FIG. 16, mouse immunoglobulins are added to the capturing zone (164). The mouse immunoglobulins interact with HAMA, and keep it from affecting the accuracy of the test.

In the embodiments where the capturing reagent is located in a capturing zone upstream of the sample application zone, the capturing reagent will have preferably been pre-loaded and dried onto the test strip and is eluted and carried by the elution medium to the sample application zone, where it interacts and captures an interfering substance. The capturing reagent is preferably soluble in the elution medium and the capturing reagent is solubilized and mobilized upon contact with the elution medium. In some preferred embodiments, the capturing reagent has been dried into the test strip. In other preferred embodiments, the capturing reagent may be pre-dried by freeze drying or lyophilizing and then pre-loaded into the test strip. In other embodiments, the capturing reagent may be absorbed, adsorbed, embedded or trapped on the test strip. When elution medium reaches the capturing reagent in the capturing zone, the mobile capturing reagent is suspended and travels with the elution medium.

As an interfering substance, e.g. a human anti-mouse antibody (HAMA), is also capable of forming a complex with the labeled, non-immobilized reagent of the reagent zone and the immobilized analyte binding partner of the detection zone, thus indicating a positive test result in the immunoassay (FIG. 3), the carrier further preferably includes at least one capturing zone. Each capturing zone contains a capturing reagent specifically interacts with a certain interfering substance, thereby immobilizing the interfering substance in the capturing zone. As the capturing zone is separated from the detection zone by space, and the sample starts to migrate over the reagent zone and the capturing zone before reaching the carrier's detection zone, the method allows a separation of the interfering substance from the analyte of interest (FIG. 4). In some embodiments, the capturing zone is located between the reagent zone and the detection zone. In other embodiments, the capturing zone may also be located between the sample application zone and the reagent zone.

In a preferred embodiment, the capturing zone is located upstream of the sample application zone, as shown in FIGS. 12-15.

In some preferred embodiments, the invention is in the form of a test kit for the detection of adenovirus using a sample obtained from a patient's eye, preferably using a collection device such as a sterile swab member. If such a collection device is used (see example shown in FIG. 8), it is preferably made out of a bibulous material, for example Dacron® fibers, or highly purified cotton fibers, which are preferably fixed to the plastic device by ultrasonic welding. Alternative materials may be polyester, rayon, polyamide or other fibrous polymeric materials.

If an absorbent pad is included, a polyester fleece is preferably used for the absorbent pad and is preferably manufactured by Binzer, Hatzfeld (Federal Republic of Germany). The fleece is preferably a polyester fleece reinforced with 10% Kuralon® fibers. The thickness of the fleece preferably ranges from 1 and 2 mm, and the absorbance capacity is 1800 ml/m$^2$.

In some preferred embodiments, the application and reagent zones are preferably made of 80 parts polyester and 20 parts viscous staple fibers at a preferred thickness of 0.32 mm and an absorbing capacity of 500 ml/m$^2$. The reagent zone is preferably impregnated with the following solutions and then dried: 100 mmol/l HEPES Buffer, pH 7.5, 100 mol/l NaCl, conjugate of gold particles and anti-Hexon antibodies at a concentration that has an optical density of 10 at 520 nm. Hexon is a protein that is common in the capsid of human adenoviruses. The test gold is mixed with control gold and sprayed together onto the reagent zone. The gold sol is preferably manufactured according to standard procedures (Fres. Nature Vol. 241, p. 20-22, 1973, incorporated herein by reference). Conjugation with the antibody is preferably carried out according to prior art procedure (J. Immunol. Meth. Vol. 34, p. 11-31, 1980, incorporated herein by reference). Sample application takes place in the sample application zone.

In some preferred embodiments, the detection zone is made of a nitrocellulose (NC) membrane with a nominal pore size of 8 nm and a thickness of 100 nm (produced by Schleicher & Schuell, Germany). Alternatively, other custom prepared nitrocellulose membranes of different pore sizes (for example, nitrocellulose membranes of different pore sizes from MDI Membrane Technologies, India), preferably ranging from 3 μm to 15 μm, may be used. The test line preferably contains a Hexon specific antibody (not labeled) which is specific for a different epitope than the antibody conjugated to the gold. The control zone preferably contains a totally unrelated species, for example Rabbit anti chicken antibody or antigen, that binds to the control conjugate when Chicken IgY is conjugated to the gold. If the test works correctly, the control line will appear even if Hexon is not present.

The interfering substances are preferably removed by incorporating capturing reagents at a variety of positions and configurations. Some examples of the capturing reagents that could be used include, but are not limited to, Mouse Immunoglobulins (for example immunoglobulins obtained from Millipore Corporation, Massachusetts), TRU Block™ blocking reagent (Meridian Life Science, Inc, Ohio), heterophilic blocking agents, for example, Heterophilic Blocking Reagents (HBR) from Scantibodies Laboratory, Inc. (California). The capturing reagents may be in the elution medium, mixed and dried with the reagents, incorporated into the sample application zone, incorporated into the sample collector fleece material, located upstream of the sample application zone and/or can be immobilized on the nitrocellulose either as a line or a zone. Any of these or combinations of these may be used depending on the test and sample matrix.

The chromatographic materials are preferably in communication with each other by overlapping with each other in order to create a fluid pathway.

In some preferred embodiments, instead of lysing cells "outside" of a point-of-care testing device, the present invention utilizes "in situ lysis". The term "in situ lysis", as used herein, describes techniques for incorporating lysis agents into a point-of-care testing device, such as a chromatography test strip or other lateral flow immunoassay device, so that the lysis operation is not conducted as a separate step.

In these embodiments, the methods and devices of the present invention incorporate a lysis zone including at least one lysis agent as part of a lateral flow immunoassay test strip, such as those discussed herein, or other lateral flow immunoassay devices known in the art, in order to lyse the sample material in situ. In addition, a capturing zone captures interfering substances to increase the accuracy of the assay.

The present invention is suitable for various methods of loading the sample. The assay will either be started directly when sample is transferred in a sufficient volume of liquid, such as a body fluid, or the process may require that a sample be added to or eluted by a sample transport liquid (e.g. tap water or a buffer solution). In one preferred embodiment, a sample which has been collected, such as by a swab, is transferred directly onto the sample application zone of a test strip. In this embodiment, a sample transport liquid is then added to the test strip. In another preferred embodiment, a liquid sample is deposited directly onto the sample application zone of a test strip. In this embodiment, the liquid sample itself, if of sufficient volume, becomes the transport liquid. If the volume of the liquid sample is insufficient, then a sample transport liquid is additionally added. In yet another preferred embodiment, a liquid sample is pre-mixed with the sample transport liquid and then both are applied to the test strip together.

Following sample loading, sample traveling with the transport liquid encounters the lysis agent. The lysis agent will have been pre-loaded onto the test strip and is eluted by the transport liquid. In some preferred embodiments, the lysis agent has been dried into the test strip. Alternatively, the lysis agent may be pre-dried by freeze drying or lyophilizing and then pre-loaded into the test strip. In other embodiments, the lysis agent may be absorbed, adsorbed, embedded or trapped on the test strip. In a preferred embodiment, the lysis agent is localized between the sample application zone and the reagent zone. The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in the sample, then being exposed in suspension to the lysis agent, are themselves lysed in situ. The elution medium then carries the analyte, including any lysis-freed components, through the reagent and capturing zones and to the detection zone.

The location where the lysis agent is pre-loaded can be varied as needed. In order to maximize the time that the sample has to interact with the lysis agent as well as to minimize the amount of lysis agent reaching the detection zone, the dried, absorbed, adsorbed, embedded, or trapped lysis agent may be located in or just downstream of the sample application zone. Or, in order to minimize the distance in which the lysed product must travel before reaching the reagent zone, the lysis agent may be located closer to the reagent zone.

The concentration of lysis agent pre-loaded onto a test strip is preferably between 0.001% and 5% weight/volume. The volume to be pre-loaded depends on where the lysis agent is pre-loaded. Appropriate ranges are 1 to 10 microliters when pre-loaded into the sample collector fleece (the sample application zone) or 5 to 50 microliters when pre-loaded into the absorbent pad or into other locations within the test strip. Ideally, the amount pre-loaded should be approximately 3 microliters pre-loaded into the sample collector fleece or approximately 10 microliters pre-loaded into the absorbent pad or into other locations within the test strip.

Selection of a specific lysing environment and agent will depend on the analyte and the assay. pH and ionic strength are key to the lysing environment. As to pH established by the lysis agent, a pH below 4.0 tends to precipitate materials, especially proteins. Higher pH, above approximately 10.0, tends to lyse materials such as proteins and cells walls. Therefore, a pH of approximately 10.0 or above is preferable for many applications. Alternatively, lower pH may be preferred for nucleic acid targets.

As to ionic strength established by the lysis agent, both high and low ionic strength may be used to lyse. For example, a lower ionic strength (hypotonic) tends to break up erythrocytes. Water by itself can lyse erythrocytes. Higher ionic strength environments may be used to rupture certain cell walls and membranes.

As to specific lysis agents, they may be grouped and selected based on their properties: salts, amphoteric and cationic agents, ionic and non-ionic detergents. The salt, Ammonium Chloride ($NH_4Cl$), lyses erythrocytes. Other salts, including, but not limited to, high concentrations of Sodium Chloride (NaCl) and Potassium Chloride (KCl), may rupture certain cell walls and membranes. Other lysis agents are amphoteric agents including, but not limited to, Lyso PC, CHAPS, and Zwittergent. Alternatively, cationic agents including, but not limited to, C16 TAB and Benzalkonium Chloride may be used as a lysis agent. Both ionic and non-ionic detergents are often used to break or lyse the cell wall or cell membrane components such as lipoproteins and glycoproteins. Common ionic detergents include, but are not limited to, SDS, Cholate, and Deoxycholate. Ionic detergents are good solubilizing agents. Antibodies retain their activity in 0.1% SDS or less. Common non-ionic detergents include, but are not limited to, Octylglucoside, Digitonin, C 12E8, Lubrol, Triton X-100, Noniodet P-40, Tween 20, and Tween 80. Non-ionic and mild ionic detergents are weaker denaturants and often are used to solubilize membrane proteins such as viral surface proteins. Additional lysis agents include, but are not limited to, urea and enzymes. Combinations of different lysis agents may be used to optimize the lysing environment.

Surfactants are generally wetting agents and lower the surface tension of a liquid. This then allows easier spreading by lowering the interfacial tension between liquids. So, surfactants can interfere with the natural binding of antigen and antibody or ligand and receptors. The concentrations are, therefore, experimentally chosen for each class of lysis agent. Once lysis occurs, it is important that the desired binding reactions not be hindered. Generally, 0.001% lysis agent concentration is considered the lower limit, and the upper limit is approximately 1%. There is an additive or synergistic effect when combinations of lysis agents are used. This expands the working range of concentration to run from approximately 0.001% to 1%. Finally, some undesirable non-specific binding may be prevented at a Tween 20 concentration of 5%. In all cases, the total amount of lysis agent pre-loaded onto all locations of an individual test strip must be sufficient to lyse barriers to immunodetection, permitting practical operation of the test strip.

The lysis agent itself should not interfere with any other assay detector or indicator agents and thus does not interfere with any other assay interactions and reactions to such an extent as to prevent practical operation of the assay. A lysis agent should have sufficient shelf life to allow manufacture, distribution and storage before use of a test strip in point-of-care testing.

In a preferred embodiment of the present invention, the lateral flow immunoassay device of the present invention includes a sample-transporting liquid, which can be a buffer, and a chromatography test strip containing one or several fleece materials or membranes with capillary properties through which sample flows. In a device and method of the invention, it is unnecessary to lyse the cells in the sample prior to applying the sample to the test strip.

FIGS. 17 through 20 show a lysis zone (170) and a capturing zone (174) between a sample application zone (172) and the reagent zone (173) (FIGS. 17 and 19) or the reagent zone (173) between the lysis zone (170) and the capturing zone (174) (FIGS. 18 and 20) of the test strip. In either case, the lysis zone (170) either overlaps with the sample application zone (172) such that the lysis agent is pre-loaded in the sample application zone (172) (see FIGS. 19 and 20) or the lysis zone (170) is located between the sample application zone (172) and the capturing zone (174) such that the lysis agent is pre-loaded between the sample application zone (172) and the capturing zone (174) (see FIGS. 17 and 18). Thus, lysis occurs before the sample reaches the capturing zone (174). As discussed above, the capturing zone (174) includes at least one capturing reagent that interacts with at least one interfering substance to keep the interfering substance from interfering with the assay. In some preferred embodiments, the capturing reagent is immobilized in the capturing zone. In other preferred embodiments, the capturing reagent is mobile. Selection of a specific capturing reagent depends on the analyte and the assay. The detection zone (175) preferably includes at least one test line (179) and at least one control line (177).

In other embodiments, a lysis zone could be used in combination with any of the device configurations shown in FIGS. 11 through 16.

In other preferred embodiments, at least one capturing reagent is included in the elution medium. In one preferred embodiment, mouse immunoglobulins are included in the elution medium. In these embodiments, mobile capturing reagents are part of the elution medium and they are released slowly and steadily into the sample. Incorporating capturing reagents into the running buffer ensures slow and steady interaction with the interfering substance in the sample. In one embodiment, the mouse immunoglobulins capture HAMA, and keep it from affecting the accuracy of the test.

These embodiments could use the device configurations shown in FIGS. 1-3, 6, and 10 or known lateral flow immunoassay devices. In addition, these embodiments could be used in combination with a lysis zone, such as the lysis zone discussed herein.

In some embodiments, all of the capturing reagent is in the elution medium. In other embodiments, there may be one or more capturing reagents in the elution medium and one or more capturing reagents in one or more capturing zones (with configurations for the device as shown in FIGS. 4-5 and 11-20). Alternatively, there could be multiple capturing zones located in multiple places on the device. For example, in one embodiment, there may be one or more capturing zones located upstream of the sample application zone and one or more capturing zones located downstream of the sample application zone. As another example, there may be one or more capturing zones located upstream of the sample application zone, one or more capturing zones located downstream of the sample application zone and one or more capturing reagents included in the elution medium.

In other preferred embodiments, one or more capturing reagents are incorporated into the sample collection device, which may be completely separate from the test strip or may alternatively be somehow connected to the test strip. One example of a collection device and test strip that could be used in these embodiments is shown in FIGS. 6 through 9. Other collection devices, known in the art, including, but not limited to, swab members, could be used in these embodiments in combination with any of the test strips discussed herein. These embodiments could also be used in combination with any of the other embodiments described herein.

In preferred embodiments, the collection device is made from one or more materials including, but not limited to, Polyethylene terephthalate (PET) fibers, such as Dacron® fibers, or nylon fibers, polyester fibers, cellulose fibers, rayon fibers, calcium alginate fibers, a microengineered mechanical structure containing microcapillaries and/or microchannels, or other fabrics and meshes.

In these embodiments, the capturing reagent will have preferably been pre-loaded and dried onto the collection device. In other preferred embodiments, the capturing reagent may be pre-dried by freeze drying or lyophilizing and then pre-loaded into the test strip. In other embodiments, the capturing reagent may be absorbed, adsorbed, embedded or trapped on the collection device. The capturing reagent is preferably soluble in the elution medium and the capturing reagent is solubilized and mobilized upon contact with the elution medium. After sample collection, the capturing reagent is transferred to the sample application zone along with the sample. Similar to the other embodiments described herein, the capturing reagent interacts with an interfering substance and keeps it from interfering with the assay.

In one example of these embodiments, a collection device, such as a sample collector fleece material is manufactured to include at least one capturing reagent. The fleece is thus impregnated with the capturing reagent. The collector fleece may then be wet and then wiped on the inanimate object of interest to collect a sample. This would be particularly useful to test for drugs of abuse on inanimate objects. This activates the capturing reagent and both the sample and the capturing reagent are transferred to the test strip for performance of the assay. Similar to other embodiments, the capturing reagent interacts with the interfering substance and keeps it from interfering with the results of the assay.

As another example, a collection device such as a swab member could be used to collect bodily fluids that do not require biocompatibility of the collection device including, but not limited to, urine.

In some preferred embodiments, there may be a primary collection device, which collects a body fluid sample, and a secondary intermediary collection device, which includes the capturing reagent. Two collection devices may be particularly useful in embodiments that require sterile collection devices to collect a body fluid sample. In these embodiments, the sample is collected on the primary collection device, and then transferred to the secondary intermediary collection device, where it is subject to elution and transfer to a chromatographic test strip. The capturing reagent located on the secondary intermediary collection device is also transferred to the test strip, and interacts with the interfering substances in the sample. As an example, in testing for sexually transmitted diseases, a first swab member could be used to swab the urethra or vagina. A second sample collector fleece could then be used to wipe the swab. The second sample collector fleece would include the capturing reagents.

The present invention also discloses a test strip that keeps interfering substances from affecting the proper detection of a target/analyte. In a preferred embodiment, the test strip includes an application zone for applying the sample, a reagent zone containing reagents for detecting the analyte, a capturing zone that includes one or more capturing reagent that separates the interfering substance from the sample, a detection zone for detecting the analyte, and optionally a waste zone. The detection zone may include further sections for the detection of other analytes and at least one control section, e.g. a control line comprising an immobilized specific binding partner of an indicator substance indicating the functionality of the test strip.

In preferred embodiments, the capturing zone is located upstream of the sample application zone. In other preferred embodiments, the capturing zone is eliminated, and the capturing reagents are included as part of the elution medium. In yet other preferred embodiments, capturing reagents are incorporated into a sample collection device.

The invention further relates to a method for reducing interference in a method for detecting an analyte on a chromatographic carrier. After applying a sample to the carrier, reduction of interference can be realized by having the sample containing an interfering substance, e.g. an antibody or a low-molecular-weight compound, come into contact with at least one capturing reagent traveling along the carrier, thereby separating the analyte(s) from the interfering substance, and subsequently passing the sample to a detection zone also located on the carrier for detecting the analyte. In some preferred embodiments, the capturing reagent begins by being in a capturing zone upstream of the sample application zone. When elution medium is applied, the capturing reagent travels along the test strip until it contacts the sample, and binds with the interfering substance. In other preferred embodiments, one or more capturing reagents are incorporated into a sample collection device. In other preferred embodiments, the capturing reagent is a component of the elution medium itself, and captures the interfering substance in the sample when it elutes through the test strip.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A test kit for detecting an analyte in a sample comprising:
    a) a lateral flow chromatographic test strip comprising:
        i) an application zone, wherein the sample is applied to the application zone;
        ii) a reagent zone comprising at least one first reagent, wherein the sample and the first reagent encounter each other while a test for detecting the analyte is being performed and wherein the first reagent interacts with the analyte to form a first complex; and
        iv) a detection zone comprising at least one test zone comprising at least one second reagent, wherein the second reagent complexes with and immobilizes the analyte at the test zone and wherein the detection zone is located downstream of the application zone; and
    b) at least one sample collection system comprising at least one sample collection device and at least one mobile capturing reagent that is incorporated into at least one sample application device, wherein the mobile capturing reagent is capable of interacting with at least one interfering substance in the sample such that the capturing reagent separates the interfering substance from the analyte and keeps the interfering substance from interfering with a detection of the analyte, wherein the collection system collects the sample prior to the sample being transferred to the chromatographic test strip.

2. The test kit of claim 1, wherein the reagent zone is located upstream of the application zone.

3. The test kit of claim 1, wherein the sample collection system comprises one sample collection device and the capturing reagent is incorporated into the sample collection device.

4. The test kit of claim 1, wherein the sample collection system comprises a first sample collection device and a second sample collection device, wherein the first sample collection device collects the sample and the second sample collection device comprises the mobile capturing reagent, wherein the sample is transferred from the first sample collection device to the second sample collection device before being transferred to the chromatographic test strip.

5. A method for detecting an analyte in a sample, comprising the steps of:
    a) collecting a sample with at least one sample collection system, wherein the sample collection system comprises at least one sample collection device and at least one mobile capturing reagent that is incorporated into at least one sample collection device;
    b) applying the sample and the mobile capturing reagent to a sample application zone of a lateral flow chromatographic test strip;
    c) if at least one interfering substance is present in the sample, capturing the interfering substance, wherein the mobile capturing reagent interacts with the interfering substance to separate the interfering substance from the analyte and keep the interfering substance from interfering with a detection of the analyte; and
    d) detecting the analyte separated from the interfering substance on the lateral flow chromatographic test strip.

6. The method of claim 5, wherein the mobile capturing reagent is incorporated into the sample collection device that collects the sample.

7. The method of claim 5, wherein the sample collection system comprises a first sample collection device and a second collection device, wherein the first sample collection device collects the sample and the second collection device comprises the mobile capturing reagent, wherein the sample is transferred from the first sample collection device to the second collection device before being applied to the lateral flow chromatographic test strip.

8. The method of claim 5, wherein step d) occurs on a detection zone of the lateral flow chromatographic test strip comprising at least one test zone comprising at least one detection reagent, wherein the detection reagent complexes with and immobilizes the analyte or an antibody against the analyte at the test zone and wherein the detection zone is located downstream of the sample application zone.

* * * * *